US011304440B2

(12) United States Patent
Kudithipudi et al.

(10) Patent No.: US 11,304,440 B2
(45) Date of Patent: Apr. 19, 2022

(54) TOBACCO HAVING ALTERED LEAF PROPERTIES AND METHODS OF MAKING AND USING

(71) Applicant: ALTRIA CLIENT SERVICES LLC, Richmond, VA (US)

(72) Inventors: Chengalrayan Kudithipudi, Midlothian, VA (US); Alec J. Hayes, Chesterfield, VA (US); Marcos Fernando de Godoy Lusso, Chesterfield, VA (US); Jerry Whit Morris, Jetersville, VA (US)

(73) Assignee: Altria Client Services LLC, Richmond, VA (US)

( * ) Notice: Subject to any disclaimer, the term of this patent is extended or adjusted under 35 U.S.C. 154(b) by 44 days.

(21) Appl. No.: 16/674,838

(22) Filed: Nov. 5, 2019

(65) Prior Publication Data

US 2020/0071717 A1 Mar. 5, 2020

Related U.S. Application Data

(63) Continuation of application No. 14/681,166, filed on Apr. 8, 2015, now abandoned.

(60) Provisional application No. 61/976,680, filed on Apr. 8, 2014.

(51) Int. Cl.

| | |
|---|---|
| ***A24D 1/00*** | (2020.01) |
| ***C12N 15/82*** | (2006.01) |
| ***A24B 13/00*** | (2006.01) |
| ***A24D 3/04*** | (2006.01) |
| *A24F 40/20* | (2020.01) |

(52) U.S. Cl.

CPC ................ *A24D 1/00* (2013.01); *A24B 13/00* (2013.01); *A24D 3/043* (2013.01); *C12N 15/8218* (2013.01); *C12N 15/8243* (2013.01); *C12N 15/8261* (2013.01); *A24F 40/20* (2020.01)

(58) Field of Classification Search

CPC ............ C12N 15/8243; C12N 15/8218; C12N 15/8261; A24B 13/00; A24D 1/00; A24D 3/043

See application file for complete search history.

(56) References Cited

U.S. PATENT DOCUMENTS

| | | | |
|---|---|---|---|
| 4,516,590 | A | 5/1985 | Teng |
| 4,528,993 | A | 7/1985 | Sensabaugh, Jr. et al. |
| 4,660,577 | A | 4/1987 | Sensabaugh, Jr. et al. |
| 4,683,195 | A | 7/1987 | Mullis et al. |
| 4,683,202 | A | 7/1987 | Kary |
| 4,800,159 | A | 1/1989 | Mullis et al. |
| 4,848,373 | A | 7/1989 | Lenkey |
| 4,965,188 | A | 10/1990 | Mullis et al. |
| 5,372,149 | A | 12/1994 | Roth et al. |
| 2004/0118422 | A1 | 6/2004 | Lundin et al. |
| 2005/0178398 | A1 | 8/2005 | Breslin et al. |
| 2005/0244521 | A1 | 11/2005 | Strickland et al. |
| 2006/0191548 | A1 | 8/2006 | Strickland et al. |
| 2009/0114235 | A1 | 5/2009 | Mallmann et al. |
| 2011/0173721 | A1* | 7/2011 | Albino .................... C12N 9/00 800/286 |
| 2012/0024301 | A1 | 2/2012 | Carroll et al. |
| 2012/0031414 | A1 | 2/2012 | Atchley et al. |
| 2012/0031416 | A1 | 2/2012 | Atchley et al. |
| 2012/0052021 | A1 | 3/2012 | Gerd et al. |

FOREIGN PATENT DOCUMENTS

| | | | |
|---|---|---|---|
| CN | 102845476 | B | 1/2013 |
| EP | 2537929 | A1 | 12/2012 |
| KR | 2008-0082124 | A | 9/2008 |
| WO | WO 00/67558 | A1 | 11/2000 |
| WO | WO 2011/088180 | A1 | 7/2011 |

OTHER PUBLICATIONS

Wang, Peng, et al. "Generation of tobacco lines with widely different reduction in nicotine levels via RNA silencing approaches." Journal of biosciences 33.2 (2008): 177-184 (Year: 2008).*

Riechers, Dean E., and Michael P. Timko. "Structure and expression of the gene family encoding putrescine N-methyltransferase in Nicotiana tabacum: new clues to the evolutionary origin of cultivated tobacco." Plant molecular biology 41.3 (1999): 387-401 (Year: 1999).*

Matthew, Louisa. "RNAi for plant functional genomics." Comparative and Functional Genomics 5.3 (2004): 240-244. (Year: 2004).*

Arunraj et al., "Desiccation and topping induced silencing of 'putrescine N-methyl transferase2' regulate nicotine biosynthesis in *Nicotiana tabacum* cv. Petite Havana," *Australian Journal of Crop Science*, 8(1):109-118 (2014).

Basuki et al., "Characterization of cDNA for PMT: a Partial Nicotine Biosynthesis-Related Gene Isolated from Indonesian Local Tobacco (*Nicotiana tabacum* cv. *Sindoro1*)," *HAYATI Journal of Biosciences*, 20(4):187-195 (2013).

Biastoff et al., "Putrescine N-methyltransferase—the start for alkaloids," *Phytochemistry*, 70(15-16):1708-1718 (2009).

Dewey et al., "Molecular genetics of alkaloid biosynthesis in Nicotiana tabacum," *Phytochemistry*, 94:10-27 (2013).

European Communication dated Sep. 28, 2017, in European Patent Application No. 15719535.5, 8 pages.

Extended European Search Report dated Feb. 10, 2020, in European Patent Application No. 19187835.4, 11 pages.

Gavilano et al., "Genetic engineering of *Nicotiana tabacum* for reduced nornicotine content," *Journal of Agricultural and Food Chemistry*, 54(24):9071-9078 (2006).

Heggestad et al., "Development of Burley 21, the first wildfire-resistant tobacco variety, including results of variety trials," *Bulletin 321*, pp. 1-51 (1960).

(Continued)

*Primary Examiner* — Weihua Fan

(74) *Attorney, Agent, or Firm* — Arnold & Porter Kaye Scholer LLP

(57) ABSTRACT

This disclosure provides tobacco plants containing a PMT RNAi and tobacco plants having a mutation in PMT, and methods of making and using such plants.

20 Claims, 13 Drawing Sheets

Specification includes a Sequence Listing.

(56) References Cited

OTHER PUBLICATIONS

Hibi et al., "Gene expression in tobacco low-nicotine mutants," *Plant Cell*, 6(5):723-735 (1994).
International Preliminary Report on Patentability dated Oct. 12, 2016, in International Application No. PCT/US2015/024818, 12 pages.
International Search Report and Written Opinion dated Aug. 28, 2015, in International Application No. PCT/US2015/024818, 22 pages.
Kessler et al., "Field experiments with transformed plants reveal the sense of floral scents," *Science*, 321(5893):1200-1202 (2008).
Legg et al., "Registration of La Burley 21 Tobacco Germplasm 1 Registration (No. GP 8)," *Crop Science*, 10(2):212-212 (1970).
Ling et al., "An interspecific Nicotiana hybrid as a useful and cost-effective platform for production of animal vaccines," *PLoS One*, 7(4):e35688 (9012).
Lopez, "Developing Non-GMO Tobacco Cultivars with Lower Alkaloid Content Using a Reverse Genetics Strategy," MS Thesis, North Carolina State University, USA (2011).
McCallum et al., "Targeting Induced Local Lesions IN Genomes (TILLING) for Plant Functional Genomics," *Nat. Biotechnol.*, 18:455-457 (2000).
Miller el al., "A grade index for type 22 and 23 fire-cured tobacco," *Tobacco International*, 192(22):55-57 (1990).
Mizusaki et al., "Phytochemical studies on tobacco alkaloids XIV. The occurrence and properties of putrescine N-metlyltransferase in tobacco roots," *Plant and Cell Physiology*, 12(4):633-640 (1971).
Nielsen et al., "Registration of HI and LI Burley 21 Tobacco Germplasms," *Crop Science*, 28(1):206-207 (1988).
Official Standard Grades for Flue-Cured Tobacco (U.S. Types 11, 12, 13, 14 and Foreign Type 92), effective Mar. 27, 1989 (54 F.R. 7925).
Rigola et al., "High-throughput detection of induced mutations and natural variation using KeyPoint™ technology," *PloS One*, 4(3):e4761 (2009).
Ruiz et al., "Preliminarv studies on the influence of boron on the foliar biomass and quality of tobacco leaves subjected to $NO3^-$ fertilization," *Journal of the Science ofFood and Agriculture*, 81(8):739-744 (2001).
Sun et al., "Genetic variation in alkaloid accumulation in leaves of Nicotiana," *Journal of Zhejiang University Science B*, 14(12):1100-1109 (2013).
Townsend el al., "High-frequency modification of plant genes using engineered zinc-finger nucleases," *Nature*, 459(7245):442-445 (2009).
Voytas, "Plant genome engineering with sequence-specific nucleases," *Annual Review of Plant Biology*, 64:327-350 (2013).
Wang et al., "Generation of tobacco lines with widely different reduction in nicotine levels via RNA silencing approaches," *Journal of Biosciences*, 33(2):177-184 (2008).

* cited by examiner

Figure 1 - Continued
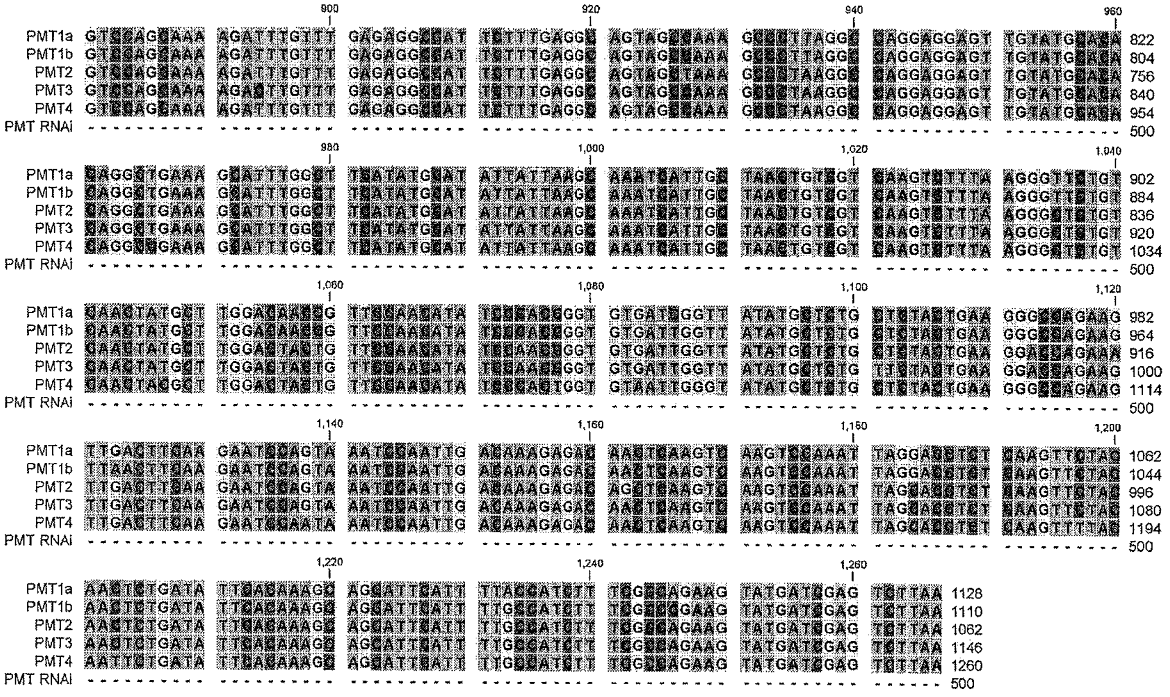

Figure 4

```
20 40 60
ATG GAA GTC ATA TCT ACC AAC ACA AAT GGC TCT ACT ATC TTC AAG AAT GGT GCC ATT CCC ATG AAC GGT TAC CAG
 M   E   V   I   S   T   N   T   N   G   S   T   I   F   K   N   G   A   I   P   M   N   G   Y   Q

80 100 120 140
AAT GGC ACT TCC AAA CAC CAA AAC GGC CAC CAG AAT GGC ACT TCC GAA CAT CGG AAC GGC CAC CAG AAT GGG ATT
 N   G   T   S   K   H   Q   N   G   H   Q   N   G   T   S   E   H   R   N   G   H   Q   N   G   I

160 180 200 220
TCC GAA CAC CAA AAC GGC CAC CAG AAT GGC ACT TCC GAG CAT CAG AAC GGC CAT CAG AAT GGG ACA ATC AGC CAT
 S   E   H   Q   N   G   H   Q   N   G   T   S   E   H   Q   N   G   H   Q   N   G   T   I   S   H

240 260 280 300
GAC AAC GGC AAC GAG CTA CAG CTA CTG GGA AGC TCC AAC TCT ATT AAG CCT GGT TGG TTT TCA GAG TTT AGC GCA
 D   N   G   N   E   L   Q   L   L   G   S   S   N   S   I   K   P   G   W   F   S   E   F   S   A

320 340 360
TTA TGG CCA GGT GAA GCA TTC TCA CTT AAG GTT GAG AAG TTA CTA TTC CAG GGG AAG TCT GAT TAC CAA GAT GTC
 L   W   P   G   E   A   F   S   L   K   V   E   K   L   L   F   Q   G   K   S   D   Y   Q   D   V

380 400 420 440
ATG CTC TTT GAG TCA GCA ACA TAT GGG AAG GTT CTG ACT TTG GAT GGA GCA ATT CAA CAC ACA GAG AAT GGT GGA
 M   L   F   E   S   A   T   Y   G   K   V   L   T   L   D   G   A   I   Q   H   T   E   N   G   G

460 480 500 520
TTT CCA TAC ACT GAA ATG ATT GTT CAT CTT CCA CTT GGT TCC ATC CCA AAC CCT AAA AAG GTT TTG ATC ATC GGC
 F   P   Y   T   E   M   I   V   H   L   P   L   G   S   I   P   N   P   K   K   V   L   I   I   G

540 560 580 600
GGA GGA ATT GGT TTT ACA TTA TTC GAA ATG CTT CGT TAT CCT ACA ATC GAA AAA ATT GAC ATT GTT GAG ATC GAT
 G   G   I   G   F   T   L   F   E   M   L   R   Y   P   T   I   E   K   I   D   I   V   E   I   D

620 640 660
GAC GTG GTA GTT GAT GTA TCT AGA AAA TTT TTC CCT TAT CTT GCT GCT AAT TTT AGC GAT CCT CGT GTA ACC CTA
 D   V   V   V   D   V   S   R   K   F   F   P   Y   L   A   A   N   F   S   D   P   R   V   T   L

680 700 720 740
GTC CTT GGA GAT GGG GCT GCA TTT GTA AAG GCC GCA CAA GCA GGA TAT TAT GAT GCT ATT ATA GTG GAC TCT TCT
 V   L   G   D   G   A   A   F   V   K   A   A   Q   A   G   Y   Y   D   A   I   I   V   D   S   S

760 780 800 820
GAT CCC ATT GGT CCA GCA AAA GAC TTG TTT GAG AGG CCA TTC TTT GAG GCA GTA GCC AAA GCC CTA AGG CCA GGA
 D   P   I   G   P   A   K   D   L   F   E   R   P   F   F   E   A   V   A   K   A   L   R   P   G

840 860 880 900
GGA GTT GTA TGC ACA CAG GCT GAA AGC ATT TGG CTT CAT ATG CAT ATT ATT AAG CAA ATC ATT GCT AAC TGT CGT
 G   V   V   C   T   Q   A   E   S   I   W   L   H   M   H   I   I   K   Q   I   I   A   N   C   R

920 940 960
CAA GTC TTT AAG GGC TCT GTC AAC TAT GCT TGG ACT ACT GTT CCA ACA TAT CCA ACC GGT GTG ATT GGT TAT ATG
 Q   V   F   K   G   S   V   N   Y   A   W   T   T   V   P   T   Y   P   T   G   V   I   G   Y   M

980 1,000 1,020 1,040
CTC TGT TCT ACT GAA GGA CCA GAA GTT GAC TTC AAG AAT CCA GTA AAT CCA ATT GAC AAA GAG ACA ACT CAA GTC
 L   C   S   T   E   G   P   E   V   D   F   K   N   P   V   N   P   I   D   K   E   T   T   Q   V

1,060 1,080 1,100 1,120
AAG TCC AAA TTA GCA CCT CTC AAG TTC TAC AAC TCT GAT ATT CAC AAA GCA GCA TTC ATT TTG CCA TCT TTC GCC
 K   S   K   L   A   P   L   K   F   Y   N   S   D   I   H   K   A   A   F   I   L   P   S   F   A

1,140
AGA AGT ATG ATC GAG TCT TAA
 R   S   M   I   E   S   *
```

TOBACCO HAVING ALTERED LEAF PROPERTIES AND METHODS OF MAKING AND USING

CROSS-REFERENCE TO RELATED APPLICATIONS AND INCORPORATION OF SEQUENCE LISTING

This application is a continuation of U.S. patent application Ser. No. 14/681,166, filed Apr. 8, 2015, which claims the benefit of U.S. Provisional Application No. 61/976,680, filed Apr. 8, 2014, which is incorporated by reference in its entirety herein. A sequence listing contained in the file named "P34631US02_SL.TXT" which is 28,685 bytes (measured in MS-Windows®) and created on Nov. 5, 2019, is filed electronically herewith and incorporated by reference in its entirety.

TECHNICAL FIELD

This disclosure generally relates to transgenic or mutant *Nicotiana tabacum* plants and methods of making and using such plants.

BACKGROUND

Nicotine is an abundant alkaloid (90-95%) present in cultivated tobacco. The remaining alkaloid fraction is primarily comprised of three additional alkaloids: nornicotine, anabasine, and anatabine. One of the initial steps in the biosynthesis of nicotine is the conversion of putrescine to N-methylputrescine by putrescine N-methyltransferase (PMT).

This disclosure describes methods of modulating the expression and/or activity of PMT to thereby reduce the amount of nicotine in the leaf.

SUMMARY

Provided herein are transgenic tobacco plants comprising a PMT RNAi and tobacco plants having a mutation in the gene encoding PMT, as well as methods of making and using such plants.

In one aspect, a RNA nucleic acid molecule is provided that includes a first nucleic acid between 15 and 500 nucleotides in length and a second nucleic acid between 15 and 500 nucleotides in length. Generally, the first nucleic acid has a region of complementarity to the second nucleic acid, and the first nucleic acid comprises at least 15 contiguous nucleotides of the sequence shown in SEQ ID NO:1, 3, 5, 7 or 9.

In some embodiments, the second nucleic acid hybridizes under stringent conditions to a portion of the sequence shown in SEQ ID NO:1, 3, 5, 7 or 9. In some embodiments, the region of complementarity is at least 19 nucleotides in length, or at least 100 nucleotides in length. In some embodiments, the nucleic acid molecule further includes a spacer nucleic acid between the first nucleic acid and the second nucleic acid.

In one aspect, a construct is provided that includes a first RNA nucleic acid molecule having a length of 15 to 500 nucleotides and having at least 95% sequence identity to a nucleic acid shown in SEQ ID NO:1, 3, 5, 7 or 9. In some embodiments, the construct further includes a second RNA nucleic acid molecule that has complementarity to the first RNA nucleic acid molecule. In some embodiments, the construct further includes a spacer nucleic acid between the first and second RNA nucleic acid molecule.

In one aspect, a method of making a *Nicotiana tabacum* plant is provided. Such a method typically includes transforming *N. tabacum* cells with a nucleic acid molecule described herein or a construct described herein to produce transgenic *N. tabacum* cells; regenerating transgenic *N. tabacum* plants from the transgenic *N. tabacum* cells; and selecting at least one transgenic *N. tabacum* plant that comprises the nucleic acid molecule or the construct. Such a method can further include identifying at least one transgenic *N. tabacum* plant having reduced amount of nicotine relative to a *N. tabacum* plant not transformed with the nucleic acid molecule. Such a method can further include identifying at least one transgenic *N. tabacum* plant that, when material from the at least one transgenic *N. tabacum* plant is cured, exhibits a reduced amount of at least one TSNA relative to cured material from a *N. tabacum* plant not transformed with the nucleic acid molecule.

In some embodiments, leaf from the selected transgenic *N. tabacum* plant exhibits comparable or better quality than leaf from the non-transformed *N. tabacum* plant. In some embodiments, the *N. tabacum* plant is a Burley type, a dark type, a flue-cured type, or an Oriental type.

In another aspect, a transgenic *Nicotiana tabacum* plant is provided that includes a vector. Typically, the vector includes a RNA nucleic acid molecule having a length of 15 to 500 nucleotides and having at least 95% sequence identity to a PMT nucleic acid shown in SEQ ID NO:1, 3, 5, 7 or 9. Such a transgenic *N. tabacum* plant typically exhibits reduced amount of nicotine in the leaf relative to leaf from a *N. tabacum* plant lacking the nucleic acid molecule. Such a transgenic *N. tabacum* plant, when material from the at least one transgenic *N. tabacum* plant is cured, typically exhibits a reduced amount of at least one TSNA relative to cured material from a *N. tabacum* plant lacking the nucleic acid molecule. In some embodiments, leaf from the transgenic plant exhibits comparable or better quality than leaf from a *N. tabacum* plant lacking the nucleic acid molecule.

Cured leaf is provided from any of the transgenic *N. tabacum* plants described herein. A tobacco product also is provided that includes such cured leaf. Representative tobacco products include, without limitation, cigarettes, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

In one aspect, a method of making a *Nicotiana tabacum* plant is provided. Such a method typically includes inducing mutagenesis in *N. tabacum* cells to produce mutagenized *N. tabacum* cells; obtaining one or more *N. tabacum* plants from the mutagenized *N. tabacum* cells; and identifying at least one of the *N. tabacum* plants that comprises a mutated PMT sequence. Such a method can further include identifying at least one of the *N. tabacum* plants that exhibits reduced amounts of nicotine relative to a *N. tabacum* plant lacking a mutated PMT. Such a method can further include identifying at least one of the *N. tabacum* plants that, when material from the at least one plant is cured, exhibits a reduced amount of at least one TSNA relative to cured material from a *N. tabacum* plant lacking a mutated PMT.

In some embodiments, leaf from the mutant *N. tabacum* plant exhibits comparable or better quality than leaf from the plant lacking a mutated PMT sequence. In some embodiments, the *N. tabacum* plant is a Burley type, a dark type, a flue-cured type, or an Oriental type.

In one aspect, a variety of *Nicotiana tabacum* is provided. Generally, the variety includes plants having a mutation in an endogenous nucleic acid, where the wild type endogenous nucleic acid encodes the PMT sequence shown in SEQ ID NO:2, 4, 6, 8 or 10. Typically, leaf from the mutant plants exhibits a reduced amount of nicotine relative to leaf from a plant lacking the mutation. Generally, material from the mutant plants, when cured, exhibits a reduced amount of at least one TSNA relative to cured material from a plant lacking the mutation. In some embodiments, leaf from the mutant *N. tabacum* plant exhibits comparable or better quality than leaf from the plant lacking a mutated PMT sequence.

In another aspect, cured leaf is provided from any of the *N. tabacum* varieties described herein. A tobacco product also is provided that includes the cured leaf. In some embodiments, the tobacco product includes, without limitation, cigarettes, smokeless tobacco products, tobacco-derived nicotine products, cigarillos, non-ventilated recess filter cigarettes, vented recess filter cigarettes, cigars, snuff, electronic cigarettes, e-vapor products, pipe tobacco, cigar tobacco, cigarette tobacco, chewing tobacco, leaf tobacco, shredded tobacco, and cut tobacco.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 4 shows the nucleotide and amino acid sequence of PMT3 (SEQ ID NOs: 7 and 8, respectively), with highlighting to show representative mutation sites into which a stop codon can be introduced.

DETAILED DESCRIPTION

Figure 1:
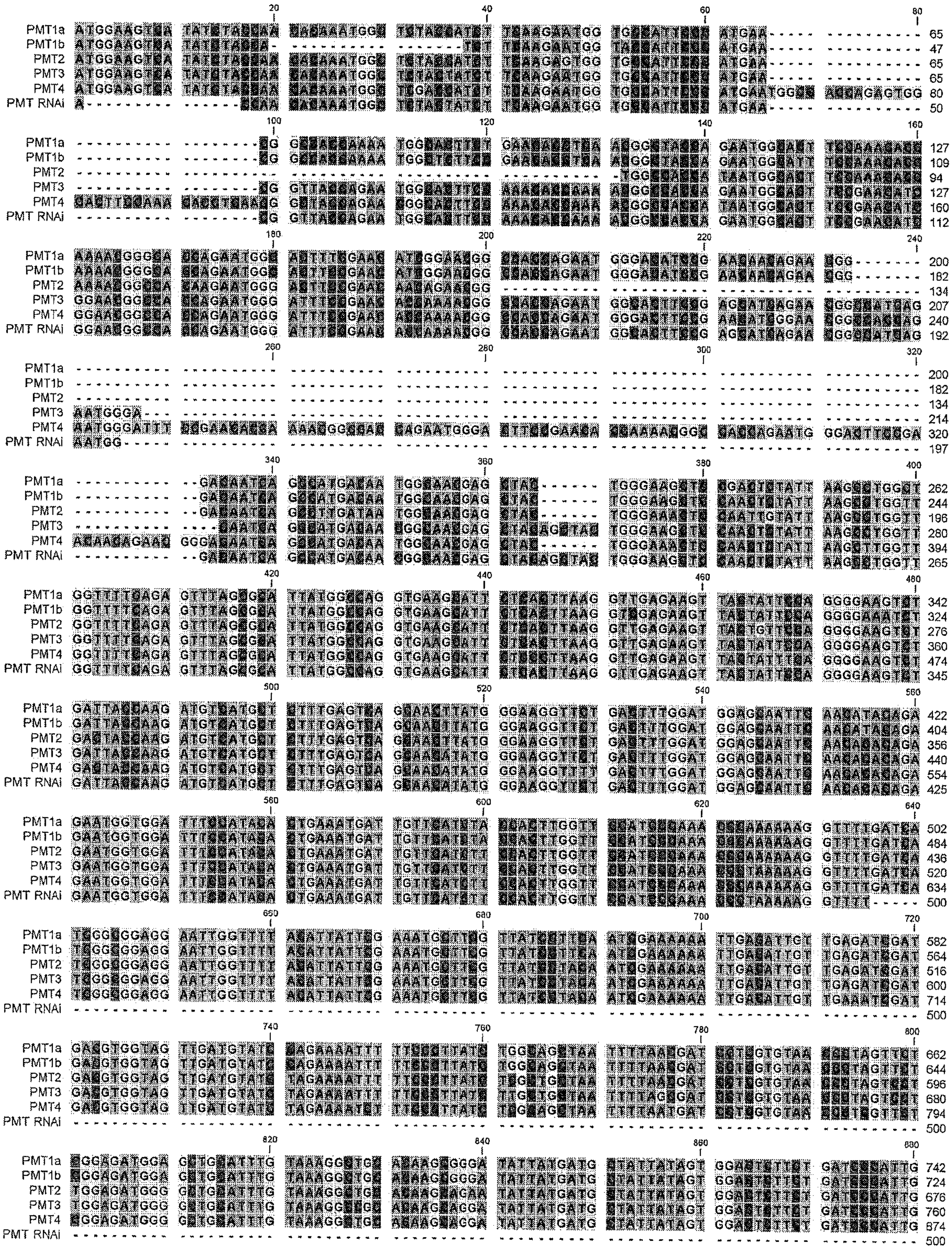
FIG. 1 is an alignment of PMT nucleotide sequences.

Nicotine biosynthesis begins with the methylation of the polyamine, putrescine, to N-methylputrescine by the enzyme, putrescine N-methyltransferase (PMT), using S-adenosylmethionine as the co-factor. This is the first step that commits precursor metabolites to nicotine biosynthesis. See, for example, Mizusaki et al., 1971, *Plant Cell Physiol.,* 12:633-40. PMT enzymes are classified under the enzyme classification system as EC 2.1.1.53. In the tobacco genome, there are known to be five genes that encode putrescine N-methyltransferases, designated PMT1a, PMT1b, PMT2, PMT3, and PMT4.

The present disclosure describes several different approaches that can be used to significantly reduce nicotine levels in tobacco leaf while maintaining leaf quality.

PMT Nucleic Acids and Polypeptides

Nucleic acids encoding PMT1a, PMT1b, PMT2, PMT3 and PMT4 from *N. tabacum* are shown in SEQ ID NOs: 1, 3, 5, 7, and 9, respectively. Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

The sequence of the PMT1a, PMT1b, PMT2, PMT3 and PMT4 polypeptides from *N. tabacum* are shown in SEQ ID NOs: 2, 4, 6, 8, and 10, respectively. As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Nucleic acids can be detected using any number of amplification techniques (see, e.g., *PCR Primer: A Laboratory Manual,* 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization.

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is oftentimes accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

A construct, sometimes referred to as a vector, containing a nucleic acid (e.g., a coding sequence or a RNAi nucleic acid molecule) is provided. Constructs, including expression constructs (or expression vectors), are commercially available or can be produced by recombinant DNA techniques routine in the art. A construct containing a nucleic acid can have expression elements operably linked to such a nucleic acid, and further can include sequences such as those encoding a selectable marker (e.g., an antibiotic resistance gene). A construct can encode a chimeric or fusion polypeptide (i.e., a first polypeptide operatively linked to a second polypeptide). Representative first (or second) polypeptides are those that can be used in purification of the other (i.e., second (or first), respectively) polypeptide including, without limitation, 6× His tag or glutathione S-transferase (GST).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Constructs as described herein can be introduced into a host cell. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer. As used herein, "host cell" refers to the particular cell into which the nucleic acid is introduced and also includes the progeny or potential progeny of such a cell. A host cell can be any prokaryotic or eukaryotic cell. For example, nucleic acids can be introduced into bacterial cells such as *E. coli*, or into insect cells, yeast or mammalian cells (such as Chinese hamster ovary cells (CHO) or COS cells). Other suitable host cells are known to those skilled in the art.

RNA Interfering Nucleic Acids and Constructs Containing Same

RNA interference (RNAi), also called post-transcriptional gene silencing (PTGS), is a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). In transgenic plants, the use of RNAi can involve the introduction of long dsRNA (e.g., greater than 50 bps) or siRNAs (e.g., 12 to 23 bps) that have complementarity to the target gene, both of which are processed by the endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery.

A RNAi nucleic acid molecule as described herein is complementary to at least a portion of a target mRNA (i.e., a PMT mRNA), and typically is referred to as an "antisense strand". Typically, the antisense strand includes at least 15 contiguous nucleotides of the DNA sequence (e.g., the PMT nucleic acid sequence shown in SEQ ID NO:1, 3, 5, 7 or 9); it would be appreciated that the antisense strand has the "RNA equivalent" sequence of the DNA (e.g., uracils instead of thymines; ribose sugars instead of deoxyribose sugars).

A RNAi nucleic acid molecule can be, for example, 15 to 500 nucleotides in length (e.g., 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, the antisense strand (e.g., a first nucleic acid) can be accompanied by a "sense strand" (e.g., a second nucleic acid), which is complementary to the antisense strand. In the latter case, each nucleic acid (e.g., each of the sense and antisense strands) can be between 15 and 500 nucleotides in length (e.g., between 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, a spacer nucleic acid, sometimes referred to as a loop nucleic acid, can be positioned between the sense strand and the antisense strand. In some embodiments, the spacer nucleic acid can be an intron (see, for example, Wesley et al., 2001, The Plant J., 27:581-90). In some embodiments, although not required, the intron can be functional (i.e., in sense orientation; i.e., spliceable) (see, for example, Smith et al., 2000, Nature, 407:319-20). A spacer nucleic acid can be between 20 nucleotides and 1000 nucleotides in length (e.g., 25-800, 25-600, 25-400, 50-750, 50-500, 50-250, 100-700, 100-500, 100-300, 250-700, 300-600, 400-700, 500-800, 600-850, or 700-1000 nucleotides in length).

In some embodiments, a construct can be produced by operably linking a promoter that is operable in plant cells; a DNA region, that, when transcribed, produces an RNA molecule capable of forming a hairpin structure; and a DNA region involved in transcription termination and polyadenylation. It would be appreciated that the hairpin structure has two annealing RNA sequences, where one of the annealing RNA sequences of the hairpin RNA structure includes a sense sequence identical to at least 20 consecutive nucleotides of a PMT nucleotide sequence, and where the second of the annealing RNA sequences includes an antisense sequence that is identical to at least 20 consecutive nucleotides of the complement of the PMT nucleotide sequence. In addition, as indicated herein, the DNA region can include an intron (e.g., a functional intron). When present, the intron generally is located between the two annealing RNA sequences in sense orientation such that it is spliced out by the cellular machinery (e.g., the splicesome). Such a construct can be introduced into one or more plant cells to reduce the phenotypic expression of a PMT nucleic acid (e.g., a nucleic acid sequence that is normally expressed in a plant cell).

In some embodiments, a construct (e.g., an expression construct) can include an inverted-duplication of a segment of a PMT gene, where the inverted-duplication of the PMT gene segment includes a nucleotide sequence substantially identical to at least a portion of the PMT gene and the complement of the portion of the PMT gene. It would be appreciated that a single promoter can be used to drive expression of the inverted-duplication of the PMT gene segment, and that the inverted-duplication typically contains at least one copy of the portion of the PMT gene in the sense orientation. Such a construct can be introduced into one or more plant cells to delay, inhibit or otherwise reduce the expression of a PMT gene in the plant cells.

The components of a representative RNAi nucleic acid molecule directed toward PMT3 are shown below. As indicated, SEQ ID NO:11 is a sense strand to PMT3; SEQ ID NO:12 is an antisense strand to PMT3; and SEQ ID NO:13 is a spacer or loop sequence.

It would be appreciated by the skilled artisan that the region of complementarity, between the antisense strand of the RNAi and the mRNA or between the antisense strand of the RNAi and the sense strand of the RNAi, can be over the entire length of the RNAi nucleic acid molecule, or the region of complementarity can be less than the entire length of the RNAi nucleic acid molecule. For example, a region of complementarity can refer to, for example, at least 15 nucleotides in length up to, for example, 500 nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 nucleotides in length). In some embodiments, a region of complementarity can refer to, for example, at least 15 contiguous nucleotides in length up to, for example, 500 contiguous nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 contiguous nucleotides in length).

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides (or amino acid residues) between the two nucleic acids (or polypeptides) is determined. The number of identical matches is divided by the length of the aligned region (i.e., the number of aligned nucleotides (or amino acid residues)) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences (nucleic acid or polypeptide), and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps:

on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

A construct (also known as a vector) containing a RNAi nucleic acid molecule is provided. Constructs, including expression constructs, are described herein and are known to those of skill in the art. Expression elements (e.g., promoters) that can be used to drive expression of a RNAi nucleic acid molecule are known in the art and include, without limitation, constitutive promoters such as, without limitation, the cassava mosaic virus (CsMVM) promoter, the cauliflower mosaic virus (CaMV) 35S promoter, the actin promoter, or the glyceraldehyde-3-phosphate dehydrogenase promoter, or tissue-specific promoters such as, without limitation, root-specific promoters such as the putrescine N-methyl transferase (PMT) promoter or the quinolinate phosphosibosyltransferase (QPT) promoter. It would be understood by a skilled artisan that a sense strand and an antisense strand can be delivered to and expressed in a target cell on separate constructs, or the sense and antisense strands can be delivered to and expressed in a target cell on a single construct (e.g., in one transcript). As discussed herein, a RNAi nucleic acid molecule delivered and expressed on a single strand also can include a spacer nucleic acid (e.g., a loop nucleic acid) such that the RNAi forms a small hairpin (shRNA).

Transgenic Plants and Methods of Making Transgenic Plants

Transgenic *N. tabacum* plants are provided that contain a transgene encoding at least one RNAi molecule, which, when transcribed, silences PMT expression. As used herein, silencing can refer to complete elimination or essentially complete elimination of the PMT mRNA, resulting in 100% or essentially 100% reduction (e.g., greater than 95% reduction; e.g., greater than 96%, 97%, 98% or 99% reduction) in the amount of PMT polypeptide; silencing also can refer to partial elimination of the PMT mRNA (e.g., eliminating about 5%, 10%, 15%, 20%, 25%, 30%, 35%, 40%, 45%, 50% or more of the PMT mRNA), resulting in a reduction (e.g., about 5%, 10%, 15%, 20%, 25%, 30%, 35%, 40%, 45%, 50% or more, but not complete elimination) in the amount of the PMT polypeptide.

A RNAi nucleic acid molecule can be transcribed using a plant expression vector. Methods of introducing a nucleic acid (e.g., a heterologous nucleic acid) into plant cells (e.g., *N. tabacum* cells) are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols,* 2(7):1565-72)), liposome-mediated DNA uptake, or electroporation.

Following transformation, the transgenic plant cells can be regenerated into transgenic tobacco plants. The regenerated transgenic plants can be screened for the presence of the transgene (e.g., a RNAi nucleic acid molecule) and/or one or more of the resulting phenotypes (e.g., reduced amount of PMT mRNA or PMT polypeptide, reduced activity of a PMT polypeptide, reduced amount of N-methylputrescine, reduced amount of one or more other intermediates in the biosynthesis of nicotine (e.g., N-methylputrescien, N-methylA-pyrolinium), reduced amount of nicotine, and/or reduced amount of one or more TSNAs (in cured tobacco)) using methods described herein, and plants exhibiting the desired phenotype can be selected.

Methods of detecting alkaloids (e.g., N-methylputrescine, nicotine) or TSNAs, and methods of determining the amount of one or more alkaloids or TSNAs are known in the art. For example, high performance liquid chromatography (HPLC)—mass spectroscopy (MS) (HPLC-MS) or high performance thin layer chromatography (HPTLC) can be used to detect the presence of one or more alkaloids and/or determine the amount of one or more alkaloids. In addition, any number of chromatography methods (e.g., gas chromatography/thermal energy analysis (GC/TEA), liquid chromatography/mass spectrometry (LC/MS), and ion chromatography (IC)) can be used to detect the presence of one or more TSNAs and/or determine the amount of one or more TSNAs.

As used herein, "reduced" or "reduction" refers to a decrease (e.g., a statistically significant decrease), in green leaf or cured leaf, of/in one or more of the following: a) the amount of PMT mRNA; b) the amount of PMT polypeptide; c) the activity of the PMT polypeptide; d) the amount of N-methylputrescine; e) the amount of one or more other intermediates in the biosynthesis of nicotine; and/or f) the amount of nicotine. In addition, "reduced" or "reduction" refers to a decrease (e.g., a statistically significant decrease), in cured leaf, in the amount of one or more tobacco-specific nitrosamines (TSNAs; e.g., N'-nitrosonornicotine (NNN), 4-(methylnitrosoamino)-1-(3-pyridyl)-1-butanone (NNK), N'-nitrosoanatabine (NAT), N'-nitrosoanabasine (NAB), and 4-(methylnitrosoamino)-1-(3-pyridyl)-1-butanal (NNAL)). As used herein, "reduced" or "reduction" refers to a decrease in any of the above by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

Leaf from progeny plants also can be screened for the presence of the transgene and/or the resulting phenotype, and plants exhibiting the desired phenotype can be selected. As described herein, leaf from such transgenic plants exhibit a reduced amount of N-methylputrescine, a reduced amount of one or more other intermediates in the biosynthesis of nicotine, a reduced amount of nicotine, or, in cured tobacco, a reduced amount of one or more TSNAs (e.g., compared to leaf from a plant lacking or not transcribing the RNAi). As described herein, transcription of the transgene results in leaf that exhibits a reduced amount of N-methylputrescine, a reduced amount of one or more other intermediates in the biosynthesis of nicotine, a reduced amount of nicotine, or, in cured tobacco, a reduced amount of one or more TSNAs relative to leaf from a plant not transcribing the transgene. Leaf from regenerated transgenic plants can be screened for the amount of N-methylputrescine, the amount of one or more other intermediates in the biosynthesis of nicotine, the amount of nicotine, or, in cured tobacco, the amount of one or more TSNAs, and plants having leaf that exhibit a reduced amount of N-methylputrescine, a reduced amount of one or more other intermediates in the biosynthesis of nicotine, a reduced amount of nicotine, or, in cured tobacco, a reduced amount of TSNAs, compared to the amount in a leaf from a corresponding non-transgenic plant, can be selected.

Transgenic plants exhibiting the desired phenotype can be used, for example, in a breeding program. Breeding is carried out using known procedures. Successful crosses yield $F_1$ plants that are fertile and that can be backcrossed with one of the parents if desired. In some embodiments, a plant population in the $F_2$ generation is screened for the presence of a transgene and/or the resulting phenotype using standard methods (e.g., amplification, hybridization and/or chemical analysis of the leaf). Selected plants are then crossed with one of the parents and the first backcross ($BC_1$) generation plants are self-pollinated to produce a $BC_1F_2$ population that is again screened. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the transgene and exhibits variant gene expression. Breeder's seed of the selected plant can be produced using standard methods including, for example, field testing and/or chemical analyses of leaf (e.g., cured leaf).

The result of a plant breeding program using the transgenic tobacco plants described herein are novel and useful varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility where a transgene inhibits microsporogenesis and/or pollen formation, or self-incompatibility. Female parent plants having CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The tobacco plants used in the methods described herein can be a Burley type, a dark type, a flue-cured type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, Perique tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

Mutant Plants and Methods of Making

Methods of making a *N. tabacum* plant having a mutation are known in the art. Mutations can be random mutations or targeted mutations. For random mutagenesis, cells (e.g., *N. tabacum* cells) typically are mutagenized using, for example, a chemical mutagen or ionizing radiation. Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.,* 39(14):6315-25) or zinc-finger (see, for example, Wright et al., 2005, *The Plant J.,* 44:693-705). Whether random or targeted, a mutation can be a point mutation, an insertion, a deletion, a substitution, or combinations thereof, which are discussed in more detail below.

The resultant variety of *Nicotiana tabacum* includes plants having a mutation in an endogenous PMT nucleic acid (e.g., SEQ ID NOs: 1, 3, 5, 7 or 9) encoding a PMT polypeptide sequence (e.g., SEQ ID NOs: 2, 4, 6, 8 or 10). A mutation in PMT as described herein typically results in reduced expression or activity of PMT, which, in turn, results in a reduced amount of N-methylputrescine, a reduced amount of one or more other intermediates in the biosynthesis of nicotine, a reduced amount of nicotine, or, in cured tobacco, a reduced amount of one or more TSNAs in the mutant plant relative to a plant lacking the mutation.

Figure 2:
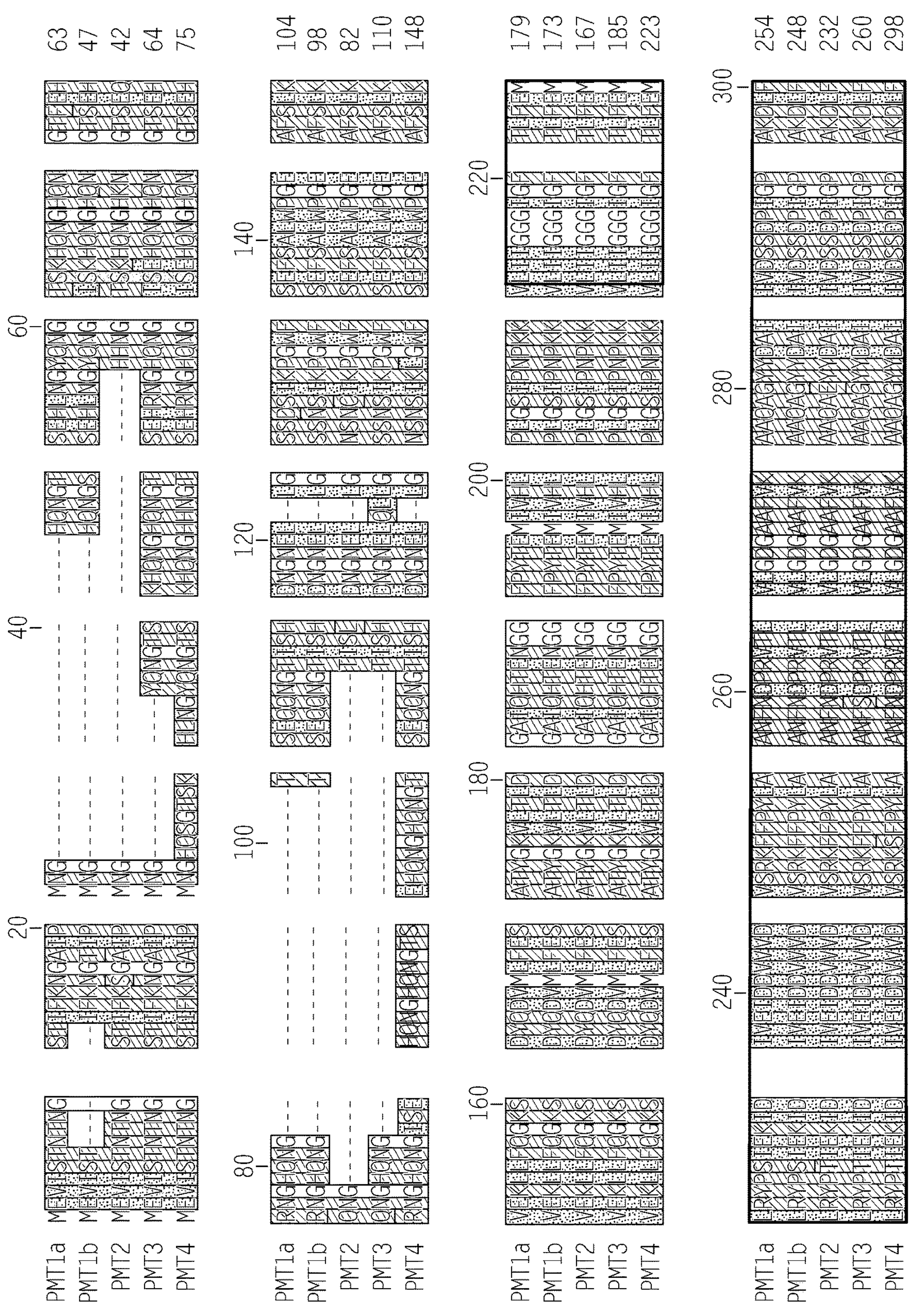
FIG. 2 is an alignment of PMT polypeptide sequences.
Figure 2:
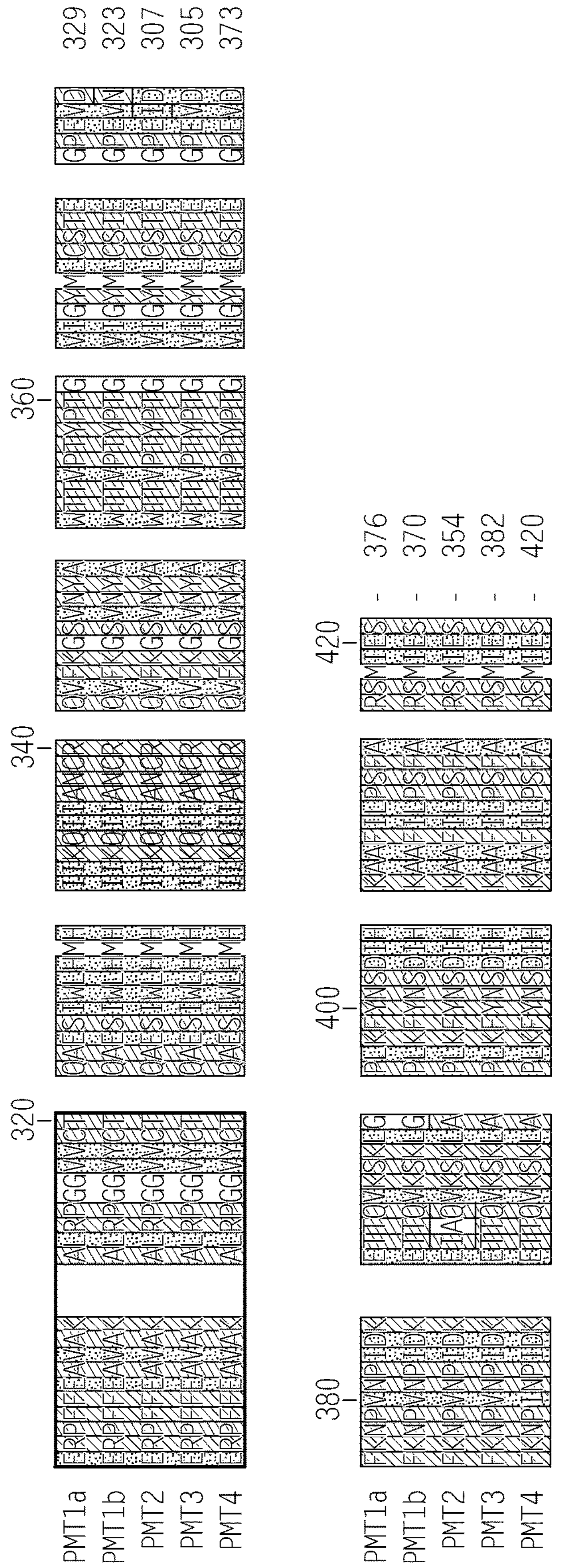

Conserved domains in polypeptides can be important for polypeptide function as well as cellular or subcellular location. FIG. 1 shows an alignment of PMT nucleic acid sequences, and FIG. 2 shows an alignment of PMT polypeptide sequences; in the polypeptide sequences shown in FIG. 2, the methyltransferase domains are indicated by a box from amino acid position 211 to amino acid position 320.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions (see, for example, the alignment shown in FIG. 2) would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Preferably, a mutation in a PMT nucleic acid results in a tobacco plant that exhibits reduced expression or activity of PMT, a reduced amount of N-methylputrescine, a reduced amount of one or more other intermediates in the biosynthesis of nicotine, a reduced amount of nicotine, or, in cured tobacco, a reduced amount of one or more TSNAs. Suitable types of mutations in a PMT coding sequence include, without limitation, insertions of nucleotides, deletions of nucleotides, or transitions or transversions in the wild-type PMT coding sequence. Mutations in the coding sequence can result in insertions of one or more amino acids, deletions of one or more amino acids, and/or conservative or non-conservative amino acid substitutions in the encoded polypeptide. In some cases, the coding sequence of a PMT comprises more than one mutation and/or more than one type of mutation.

Insertion or deletion of amino acids in a coding sequence, for example, can disrupt the conformation of the encoded polypeptide. Amino acid insertions or deletions also can disrupt sites important for recognition of binding ligand(s) or substrate(s) (e.g., putrescine, S-adenosyl-L-methionine) or for activity of the polypeptide (i.e., methyltransferase actvity). It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the PMT polypeptide, introduce a stop codon to produce a truncated polypeptide, or disrupt an active site or domain (e.g., a catalytic site or domain, a binding site or domain) within the polypeptide.

A "conservative amino acid substitution" is one in which one amino acid residue is replaced with a different amino acid residue having a similar side chain (see, for example, Dayhoff et al. (1978, in *Atlas of Protein Sequence and Structure,* 5 (Suppl. 3):345-352), which provides frequency tables for amino acid substitutions), and a non-conservative substitution is one in which an amino acid residue is replaced with an amino acid residue that does not have a similar side chain. Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Simply by way of example, a PMT3 amino acid sequence (e.g., SEQ ID NO:8) can be mutated to change phenylalanine to leucine, which may disrupt secondary structure. In addition, a PMT nucleic acid sequence (e.g., SEQ ID NO:7) can be mutated to change TGG to TAG or TGA at nucleotide positions 281, 282, 305, 306, 857, 858, 931 or 932; CAG to TAG at nucleotide positions 73, 106, 139, 172, 193, 205, 244, 349, or 841; or CAA to TAA at nucleotide positions 94, 160, 367, 430, 712, 880, 901, or 1045, each of which would result in a stop codon (see, for example, FIG. 4). Such a mutation would significantly reduce or essentially eliminate the amount of PMT mRNA or polypeptide or the activity of PMT in the plant. Similar mutations can be introduced into any of the other PMT sequences disclosed herein (e.g., PMT1a, PMT1b, PMT2, or PMT4).

Following mutagenesis, $M_0$ plants are regenerated from the mutagenized cells and those plants, or a subsequent generation of that population (e.g., $M_1$, $M_2$, $M_3$, etc.), can be screened for those carrying a mutation in a PMT sequence. Screening for plants carrying a mutation in a PMT nucleic acid or polypeptide can be performed directly using methods routine in the art (e.g., hybridization, amplification, nucleic acid sequencing, peptide sequencing, combinations thereof) or by evaluating the phenotype (e.g., reduced expression or activity of PMT, reduced amounts of N-methylputrescine, reduced amounts of one or more other intermediates in the biosynthesis of nicotine, reduced amounts of nicotine, and/or reduced amounts of one or more TSNAs (in cured tobacco)). It would be understood that the phenotype of a mutant plant (e.g., reduced expression or activity of PMT, reduced amounts of N-methylputrescine, reduced amounts of one or more other intermediates in the biosynthesis of nicotine, reduced amounts of nicotine, and/or reduced amounts of one or more TSNAs (in cured tobacco)) would be compared to a corresponding plant (e.g., having the same varietal background) that lacks the mutation.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype (e.g., reduced expression or activity of PMT, reduced amounts of N-methylputrescine, reduced amounts of one or more other intermediates in the biosynthesis of nicotine, reduced amounts of nicotine, and/or reduced amounts of one or more TSNAs (in cured tobacco)). Such plants may be heterozygous and exhibit a mutant phenotype due to a phenomenon such as dominant negative suppression, despite the presence of the wild type allele, or such plants may be homozygous due to independently induced mutations in both alleles.

As used herein, "reduced" or "reduction" refers to a decrease (e.g., a statistically significant decrease) in the expression or activity of PMT, or in the amount of N-methylputrescine, one or more other intermediates in the biosynthesis of nicotine, or nicotine, in either green or cured tobacco, or in the amount of one or more TSNAs, in cured tobacco, by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the mutation. As used herein, statistical significance refers to a p-value of less than 0.05, e.g., a p-value of less than 0.025 or a p-value of less than 0.01, using an appropriate measure of statistical significance, e.g., a one-tailed two sample t-test.

A tobacco plant carrying a mutant allele can be used in a plant breeding program to create novel and useful lines, varieties and hybrids. Desired plants that possess the mutation can be backcrossed or self-pollinated to create a second population to be screened. Backcrossing or other breeding procedures can be repeated until the desired phenotype of the recurrent parent is recovered. DNA fingerprinting, SNP or similar technologies may be used in a marker-assisted selection (MAS) breeding program to transfer or breed mutant alleles into other tobaccos, as described herein.

In some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Cured Tobacco and Tobacco Products

The methods described herein allow for leaf constituents in a tobacco plant to be altered while still maintaining high leaf quality. As described herein, altering leaf constituents refers to reducing, in green or cured leaf, the amount of N-methylputrescine, one or more other intermediates in the biosynthesis of nicotine, or nicotine, or reducing, in cured leaf, the amount of one or more TSNAs. As described herein, such methods can include the production of transgenic plants (using, e.g., RNAi or overexpression) or mutagenesis (e.g., random or targeted).

Leaf quality can be determined, for example, using an Official Standard Grade published by the Agricultural Marketing Service of the US Department of Agriculture (7

U.S.C. § 511); Legacy Tobacco Document Library (Bates Document #523267826/7833, Jul. 1, 1988, Memorandum on the Proposed Burley Tobacco Grade Index); and Miller et al., 1990, Tobacco Intern., 192:55-7. For dark-fired tobacco, leaves typically are obtained from stalk position C, and the average grade index determined based on Federal Grade and 2004 Price Support for Type 23 Western dark-fired tobacco.

Leaf from the tobacco described herein can be cured, aged, conditioned, and/or fermented. Methods of curing tobacco are well known and include, for example, air curing, fire curing, flue curing and sun curing. Aging also is known and is typically carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993; 4,660,577; 4,848,373; and 5,372,149. The tobacco also can be further processed (e.g., cut, expanded, blended, milled or comminuted), if desired, and used in a tobacco product.

Tobacco products are known in the art and include any product made or derived from tobacco that is intended for human consumption, including any component, part, or accessory of a tobacco product. Representative tobacco products include, without limitation, cigarettes, smokeless tobacco products, tobacco-derived nicotine products, cigarillos, non-ventilated recess filter cigarettes, vented recess filter cigarettes, cigars, snuff, electronic cigarettes, e-vapor products, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, sticks, rods, and the like. Representative cigarettes and other smoking articles include, for example, smoking articles that include filter elements or rod elements, where the rod element of a smokeable material can include cured tobacco within a tobacco blend. In addition to the reduced-nicotine or reduced-TSNA tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

PMT Sequences

Figure 3:
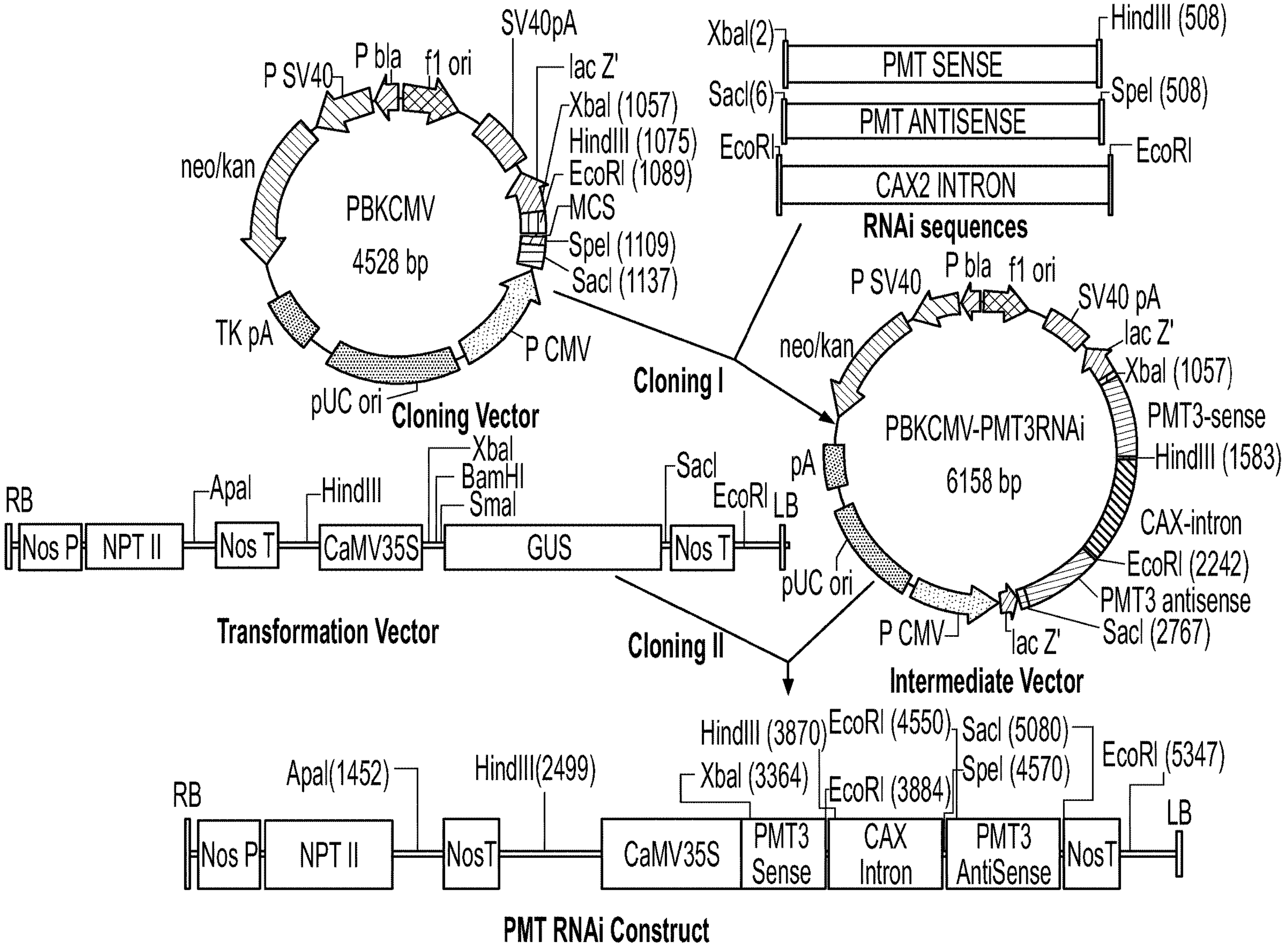
FIG. 3 is a schematic showing the RNAi construct and the cloning vector.

To develop low nicotine transgenic lines, a PMT RNAi expression vector is designed and transcribed in tobacco using the nucleic acid sequence of PMT3 (SEQ ID NO:7). The protein sequence of PMT3 is shown in SEQ ID NO:8. The cloning vector, pBK-CMV, was used for the construction of a RNAi vector containing a 500 bp sequence of PMT3 in the sense and antisense orientations (SEQ ID NOs:11 and 12, respectively). The two fragments are separated by a 660 bp tobacco Cax2 spacer sequence (SEQ ID NO:13). See FIG. 3.

```
PMT3 RNAi sense strand
                                    (SEQ ID NO: 11)
ACCAACACAAATGGCTCTACTATCTTCAAGAATGGTGCCATTCCCATGAA

CGGTTACCAGAATGGCACTTCCAAACACCAAAACGGCCACCAGAATGGCA

CTTCCGAACATCGGAACGGCCACCAGAATGGGATTTCCGAACACCAAAAC

GGCCACCAGAATGGCACTTCCGAGCATCAGAACGGCCATCAGAATGGGAC

AATCAGCCATGACAACGGCAACGAGCTACAGCTACTGGGAAGCTCCAACT

CTATTAAGCCTGGTTGGTTTTCAGAGTTTAGCGCATTATGGCCAGGTGAA

GCATTCTCACTTAAGGTTGAGAAGTTACTATTCCAGGGGAAGTCTGATTA

CCAAGATGTCATGCTCTTTGAGTCAGCAACATATGGGAAGGTTCTGACTT

TGGATGGAGCAATTCAACACACAGAGAATGGTGGATTTCCATACACTGAA

ATGATTGTTCATCTTCCACTTGGTTCCATCCCAAACCCTAAAAAGGTTTT

PMT3 RNAi antisense strand
                                    (SEQ ID NO: 12)
AAAACCTTTTTAGGGTTTGGGATGGAACCAAGTGGAAGATGAACAATCAT

TTCAGTGTATGGAAATCCACCATTCTCTGTGTGTTGAATTGCTCCATCCA

AAGTCAGAACCTTCCCATATGTTGCTGACTCAAAGAGCATGACATCTTGG

TAATCAGACTTCCCCTGGAATAGTAACTTCTCAACCTTAAGTGAGAATGC

TTCACCTGGCCATAATGCGCTAAACTCTGAAAACCAACCAGGCTTAATAG

AGTTGGAGCTTCCCAGTAGCTGTAGCTCGTTGCCGTTGTCATGGCTGATT

GTCCCATTCTGATGGCCGTTCTGATGCTCGGAAGTGCCATTCTGGTGGCC

GTTTTGGTGTTCGGAAATCCCATTCTGGTGGCCGTTCCGATGTTCGGAAG

TGCCATTCTGGTGGCCGTTTTGGTGTTTGGAAGTGCCATTCTGGTAACCG

TTCATGGGAATGGCACCATTCTTGAAGATAGTAGAGCCATTTGTGTTGGT

Cax sequence
                                    (SEQ ID NO: 13)
GAATTCGGTGAGTTCCCCCCTCCTCCCCTTTCACTTTTGTTTGTTGGTTT

CTAAGTGCTCTTTCAATTTAGAGGTTGATGTTGGGAAATAATTAAACAAT

ACTCTTGTTTTCTAAAATTTCTTGAAAACTACAATGTCTATAGAGGCAAT

ATATTTGCTTCTAAACGTTGACGGTTTTGCAAGTCTTGCGGAGGAGCTTT

GATCCAGTGTTAAAGAAATATATCATGTCTCTTATTCATCCTCCCTTTCT

TTCCTTTGTGTTTTGCTTCACTCCTGGGGTTTCAACTTTTTTCTTTCCGT

TTAACCTTTCCTTTTTTCTGCAGGATGGAACTTCAAATTACTTTAAAGGA

CTGATGCTCCTTCTCTGCTATTGATAGTTGCTGCAAGTTTCTTTGTGCAT

ATAGATCCAGAGTCTATACGTAAGTTGTGTTTCTTTTTCGTGAAATTACC

ATATGACATTGACAGCTCCTGGTCTTCGTTTTATTTATTCTTTTGGTGTT

CCTTTTAACCGATAACATCTGTTATTATTTCACTGTTACACTAATCTGCT

TTGCTTATGGTCAGTCAGTTTAGCATTAGATTAGATAACCAGTTAACCAT

TTTGGGTCTCGTTAACGTAATATTGTATTGATAACTACCTTATCATATAT

ATATCTCTGTTTTAGTGAATTC
```

Example 2

Generating a PMT Interfering RNAi

The 660 bp Cax2 sequence from BAC 57 intron 9 (SEQ ID NO:13) is cloned directly into pBK-CMK at the EcoRI site. XbaI and HindIII sites are added to the 5' and 3' ends of a 500 bp sense-orientated PMT by means of PCR with primers harboring these restriction enzyme sites.

```
PMG546F:
                                    (SEQ ID NO: 14)
ATTCTAGACCAACACAAATGGCTCTAC

PMG 546R:
                                    (SEQ ID NO: 15)
ATAAGCTTAAAACCTTTTTAGGGTTTGG
```

Similarly, BamHI and Sad sites are created at the 5' and 3' ends of the corresponding PMT antisense fragment by PCR with primers harboring these restriction enzyme sites to produce PBK-CMV-PMT RNAi plasmid.

```
PMG 547F:
                                    (SEQ ID NO: 16)
ATGAGCTCACCAACACAAATGGCTCTAC

PMG 547R:
                                    (SEQ ID NO: 17)
ATGGATCCAAAACCTTTTTAGGGTTTGG)
```

Example 3

Generating a PMT Interfering RNAi Expression Construct

To create a plant expression vector capable of mediating the constitutive transcription of PMT RNAi, the beta-glucuronidase open reading frame of the binary expression vector, pBI121 (Clontech, Palo Alto, Calif.), is excised and replaced with the 500 bp XbaI-HindIII PMT sense fragment, the 660 bp Cax2 spacer sequence cloned at the EcoRI site, and the 500 bp BamHI-Sad PMT antisense fragment by cloning into the XbaI/SacI sites of PBI121 to produce a plasmid designated PBI121-PMT RNAi. See FIG. 3.

Example 4

Production of Transgenic Plants

TN90 and K326 cultivars are transformed using Agrobacterium-mediated transformation and selected for kanamycin resistance. First generation transformants that are kanamycin-resistant are propagated in the greenhouse. At the flowering stage, plants are topped. Two weeks post-topping, the 3rd and 4th leaf from the top are collected, freeze-dried and the alkaloids are analyzed using GCMS. Relative to controls, PMT RNAi lines show significant reduction in nicotine content (Table 1). Two years of field study of selected transgenic lines and a control also show reduced nicotine content (Table 2).

TABLE 1

T0 generation of PMT RNAi transgenic plants

| Variety | Plant ID | Nicotine | Nornicotine | Anabasine | Anatabine | Total Alkaloids |
|---|---|---|---|---|---|---|
| K326 | 07T539 | 0.205 | 0.0657 | 0.0359 | 1.02 | 1.327 |
| | 07T541 | 0.213 | 0.0566 | 0.033 | 0.782 | 1.085 |
| | 07T545 | 0.216 | 0.0505 | 0.0286 | 0.65 | 0.945 |
| | 07T548 | 0.214 | 0.0384 | 0.027 | 0.56 | 0.839 |
| | 07T318 | 0.207 | 0.0349 | 0.0187 | 0.412 | 0.673 |
| | 07T331 | 0.216 | 0.0346 | 0.0212 | 0.398 | 0.67 |
| | Control | 1.53 | 0.0442 | 0.00746 | 0.0662 | 1.648 |
| TN90 | 06T348 | 0.196 | 0.0519 | 0.035 | 0.887 | 1.17 |
| | 06T347 | 0.202 | 0.0491 | 0.028 | 0.708 | 0.987 |
| | 06TN2009 | 0.197 | 0.041 | 0.0295 | 0.685 | 0.953 |
| | 06TN2083 | 0.193 | 0.0532 | 0.0276 | 0.575 | 0.849 |
| | 06TN2051 | 0.202 | 0.0522 | 0.0222 | 0.554 | 0.83 |
| | 06TN2010 | 0.213 | 0.0278 | 0.0205 | 0.528 | 0.789 |
| | Control | 3.06 | 0.07132 | 0.00871 | 0.07378 | 3.215 |

TABLE 2

Alkaloid levels in T1 and T2 generation PMT RNAi transgenic plants

| Variety | Generation | Line ID | Nicotine | Nornicotine | Anabasine | Anatabine | Total Alkaloids |
|---|---|---|---|---|---|---|---|
| K326 | T1 | T841 | 0.201 ± 0.008 | 0.031 ± 0.009 | 0.0204 ± 0.0038 | 0.319 ± 0.088 | 0.572 ± 0.10 |
| | | Control | 2.73 ± 0.46 | 0.051 ± 0.010 | 0.009 ± 0.0016 | 0.039 ± 0.007 | 2.83 ± 0.47 |
| | T2 | T841 | >0.15 ± 0.0 | 0.0250 ± 0.008 | 0.0178 ± 0.0031 | 0.371 ± 0.068 | 0.414 ± 0.08 |
| | | Control | 2.5 ± 0.28 | 0.048 ± 0.005 | 0.008 ± 0.0012 | 0.049 ± 0.006 | 2.61 ± 0.29 |
| TN90 | T1 | T841 | 0.209 ± 0.02 | 0.058 ± 0.008 | 0.033 ± 0.005 | 0.51 ± 0.163 | 0.809 ± 0.18 |
| | | Control | 4.95 ± 0.56 | 0.104 ± 0.019 | 0.014 ± 0.002 | 0.073 ± 0.011 | 5.14 ± 0.59 |

TABLE 2-continued

| Alkaloid levels in T1 and T2 generation PMT RNAi transgenic plants | | | | | | | |
|---|---|---|---|---|---|---|---|
| Variety | Generation | Line ID | Nicotine | Nornicotine | Anabasine | Anatabine | Total Alkaloids |
| | T2 | T841 | >0.15 ± 0.0 | 0.037 ± 0.015 | 0.032 ± 0.009 | 0.555 ± 0.142 | 0.635 ± 0.17 |
| | | Control | 4.12 ± 0.45 | 0.086 ± 0.012 | 0.0146 ± 0.0025 | 0.105 ± 0.014 | 4.33 ± 0.47 |

Example 5

Quality of Leaf from Transgenic Plants

Figure 6:
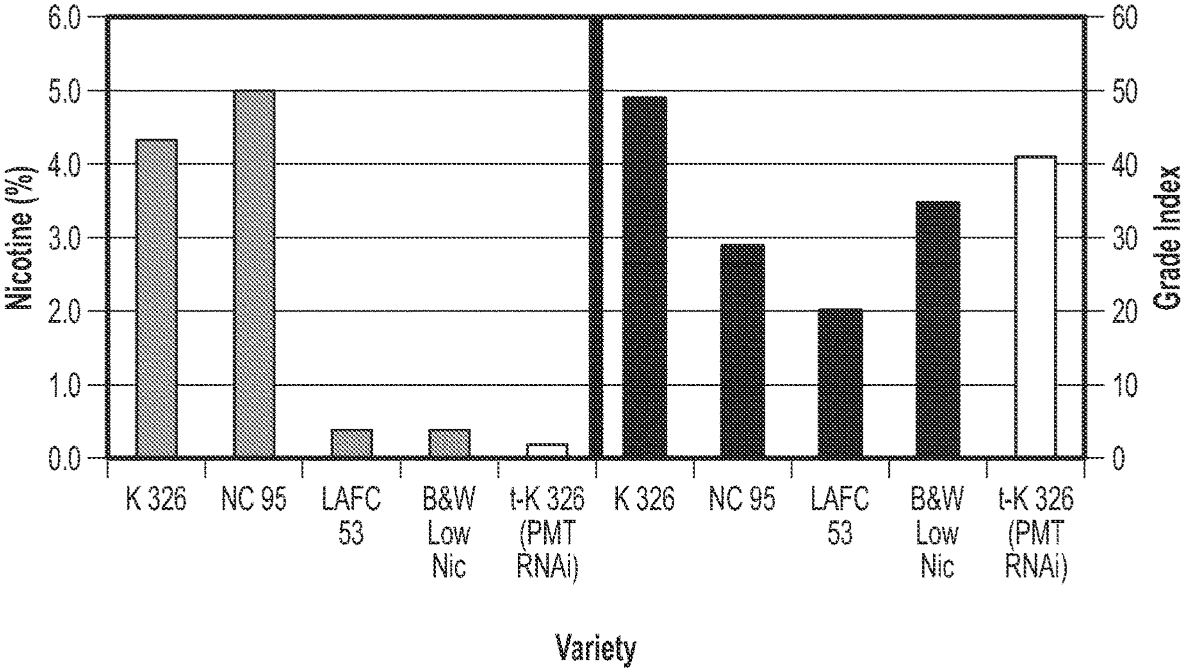
FIG. 6 shows graphs of the effect of low alkaloids on leaf quality in flue-cured varieties.
Figure 7:
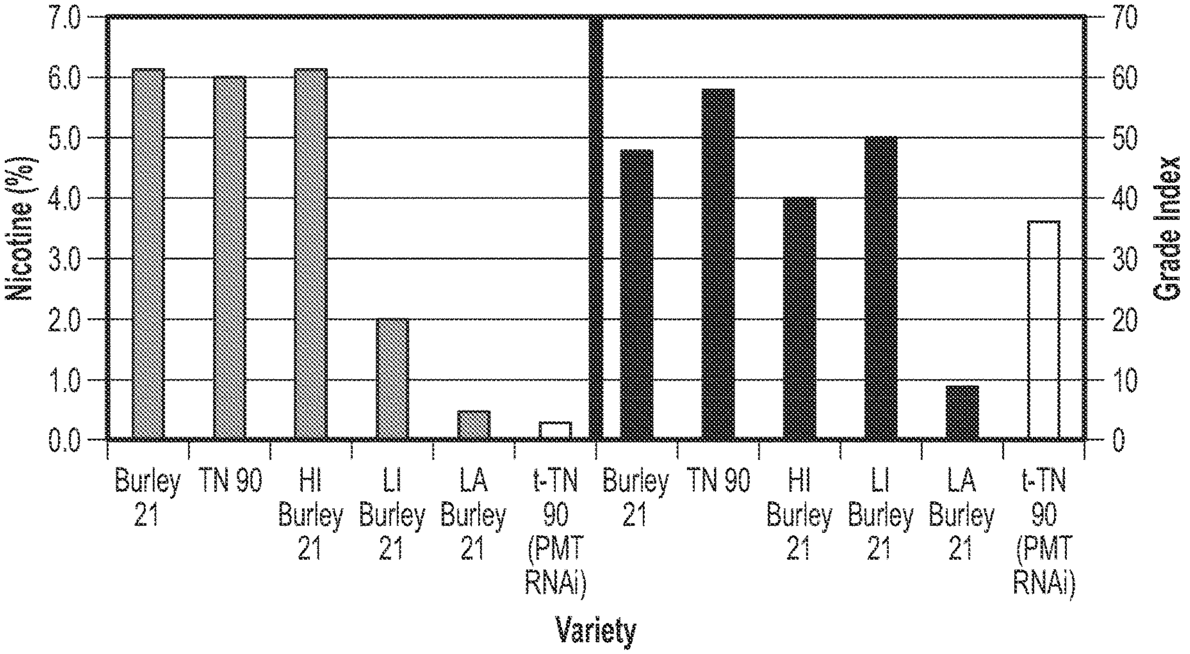
FIG. 7 shows graphs of the effect of low alkaloids on leaf quality in Burley varieties.

To compare leaf quality in existing low alkaloid tobacco lines with leaf quality in PMT-silenced lines, plants from stable K326 PMT RNAi and TN90 PMT RNAi lines along with K326, TN 90, NC 95, LAFC 53 (Ling et al., 2012, PLoS One, 7(4):e35688; referred to therein as "low pyridine alkaloid" plants (nic1nic2/aabb genotype)), B&W Low Nic, Burley 21 (Heggestad et al., 1960, University of Tennessee Agricultural Experiment Station, Bulletin 321; described therein as having reduced nicotine and nornicotine levels (nic1nic2 genotype)), HI Burley 21 or LI Burley 21 (Nielsen et al., 1988, Crop Science, 28:206; described therein as having intermediate levels of total alkaloids), and LA Burley 21 (Legg et al., 1970, Crop Science, 10:212; described therein as having "extremely low alkaloid content") are grown in 1 plot rows with 3 replications. All plants are topped at maturity, cured, and leaf samples are collected for evaluation. As demonstrated in FIGS. 6 and 7, K326 PMT RNAi and TN90 PMT RNAi lines show significantly better leaf quality compared to the other low alkaloid lines.

Figure 8:
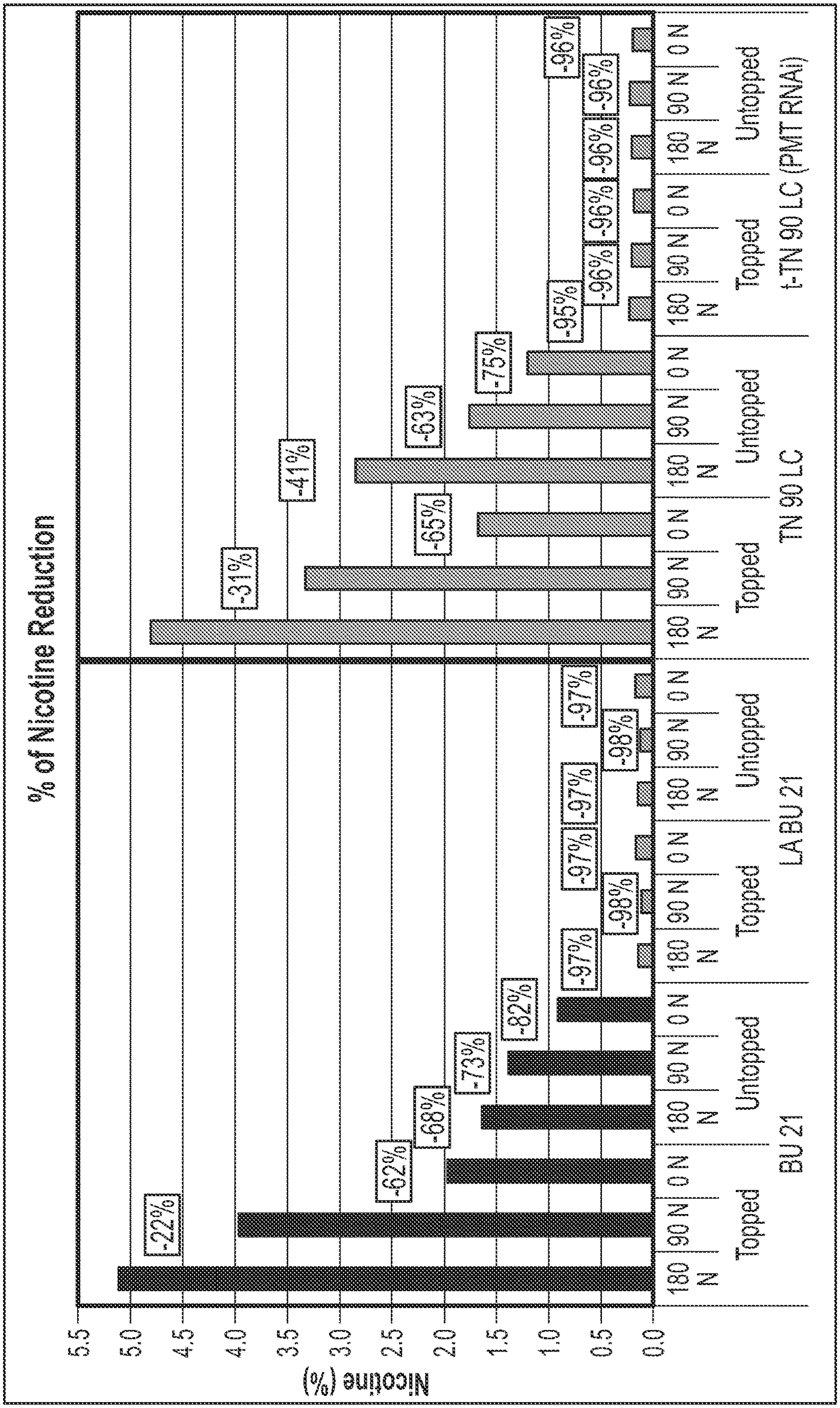
FIG. 8 is a graph showing the impact of agronomic practices on the percent nicotine reduction in select lines.
Figure 9:
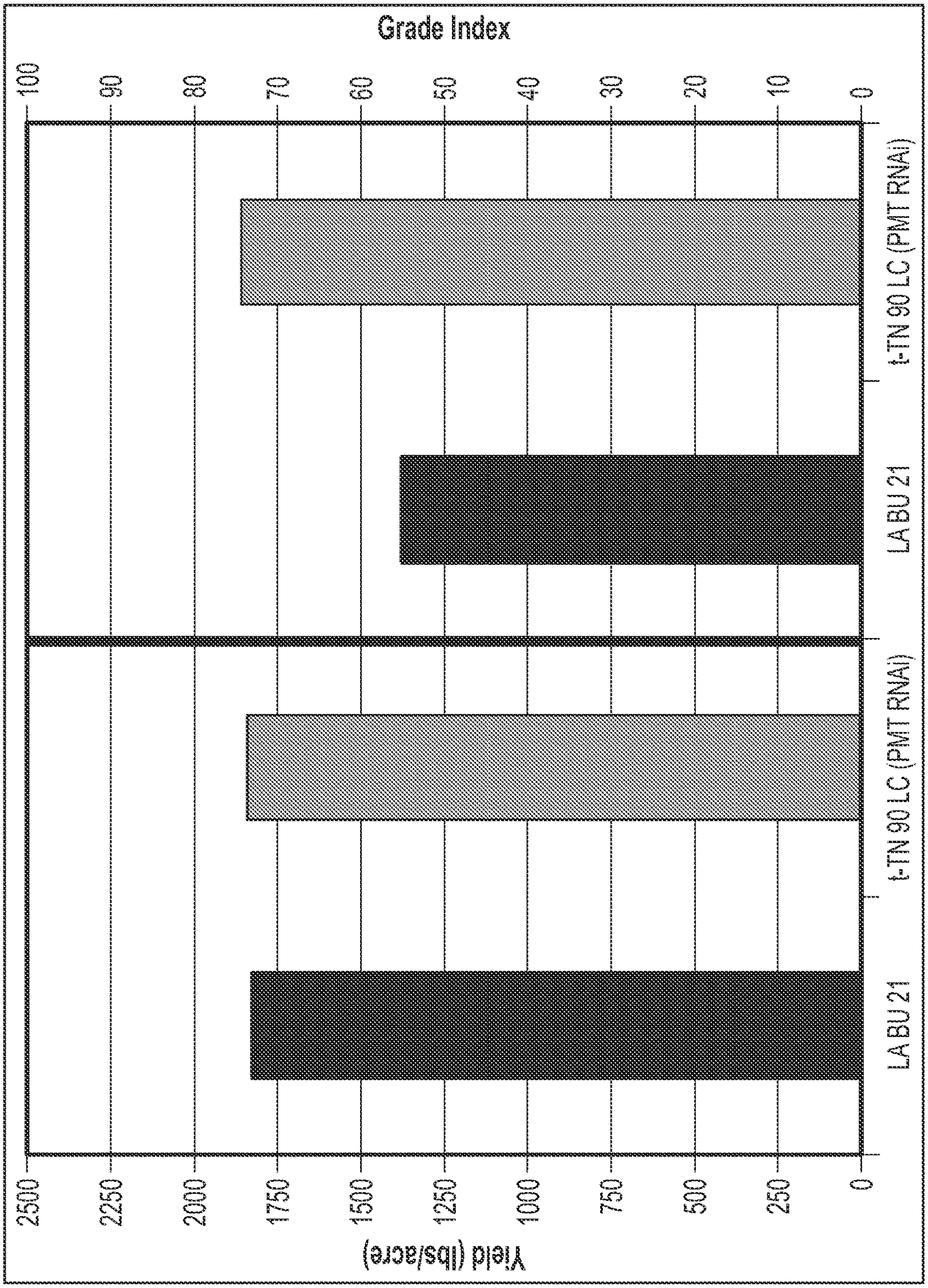
FIG. 9 is a graph showing the yield and leaf quality in a low nicotine variety and a PMT-RNAi variety.

In addition, plants from stable TN 90 LC PMT RNAi transgenic lines along with Burley 21, LA Burley 21 and TN 90 LC ("Low converter" of nicotine to nornicotine) are grown in plots in the presence of no added nitrogen (0 N), or in the presence of 90 kg/ha nitrogen (90 N) or 180 kg/ha nitrogen (180 N). Plants are topped at maturity or not, as indicated ("Topped" or "Untopped"), and leaf samples are collected after curing for evaluation. FIG. 8 shows that the TN 90 LC PMT RNAi lines exhibit a significant reduction in the amount of nicotine (%) relative to the non-transgenic plants, and also shows that the amount of nicotine in the TN 90 LC PMT RNAi lines is reduced to a level that is comparable with the LA BU 21 variety, a mutant that exhibits extremely low alkaloid content (Legg et al., 1970, Crop Science, 10:212). FIG. 9 shows that TN 90 LC PMT RNAi lines exhibit about the same yield as the LA BU 21 variety but exhibits a better leaf quality grade.

Example 6

Random Mutagenesis

A novel genetic variation in a population of tobacco plants is created to identify plants for low alkaloids. To induce random mutation, approximately 10,000 seeds of the selected tobacco variety are treated with 0.5% ethyl methane sulfonate (EMS; M1 seed), germinated and propagated (into M1 plants). M2 seeds from self-pollinated M1 plants are collected. A composite of M2 seed is grown and leaves from M2 plants are collected and the DNA extracted. Each of the five PMT sequences are amplified and sequenced, and then analyzed for mutations.

Example 7

Targeted Mutagenesis Using TALENs

Transcription activator like (TAL) effector protein sequences for the five PMT genes are designed to target either individual PMTs or all five PMTs (Table 3). The TALs are synthesized and cloned into a plant expression vector (Life Technologies, Inc.) to serve as entry vectors. Depending on the intention, three different protocols are used to generate mutagenic tobacco lines: a) one or more entry vectors containing the target TALs are directly transformed into tobacco protoplasts to generate random sequence deletion or insertion mutagenic tobacco lines; b) a donor sequence (e.g., a reporter gene such as, without limitation, the GUS gene) flanked on the left and right side with sequences that are homologous to the target insertion sequence is co-transformed into tobacco protoplasts with one or more entry vectors to generate mutagenic tobacco lines containing a target sequence interrupted by the donor sequence; or c) a donor sequence containing target TALs containing a point mutation is co-transformed into tobacco protoplasts with one or more entry vectors to generate tobacco lines having a point mutation within the target sequence.

TABLE 3

| TALEN Sequences | | | | |
|---|---|---|---|---|
| TALEN Name | Target Gene | Location* | Target Sequence | SEQ ID NO: |
| TALen 1A | All 5 PMTs | 392....448 (PMT1a) | T GAAATGATTGTTCATCTACC acttggttccatccc AAACCCAAAAAAGGTTTTG A | 18 |
| TALen 1B | All 5 PMTs | 838...893 (PMT1a) | T AAATCCAATTGACAAAGA gacaactcaagtcaa GTCCAAATTAGGACCTCTCA A | 19 |
| TALen-PMT1a | PMT1a | 62....121 | T GAACGGCCACCAAAATGG cacttctgaacacct CAACGGCTACCAGAATGGC A | 20 |

TABLE 3-continued

| TALEN Sequences | | | | |
|---|---|---|---|---|
| TALEN Name | Target Gene | Location* | Target Sequence | SEQ ID NO: |
| TALen-PMT2 | PMT2 | 57...115 | T CCCATGAATGGCCACCATAA tggcacttccaaacacca AAACGGCCACAAGAATGGG A | 21 |
| TALen-PMT3 | PMT3 | 242...290 | T ACAGCTACTGGGAAG ctccaactctattaa GCCTGGTTGGTTTTCAG A | 22 |
| TALen-PMT4 | PMT4 | 250...308 | T CCGAACACCAAAACGGCCAC cagaatgggacttccg AACACCAAAACGGCCACCAG A | 23 |

Figure 5:
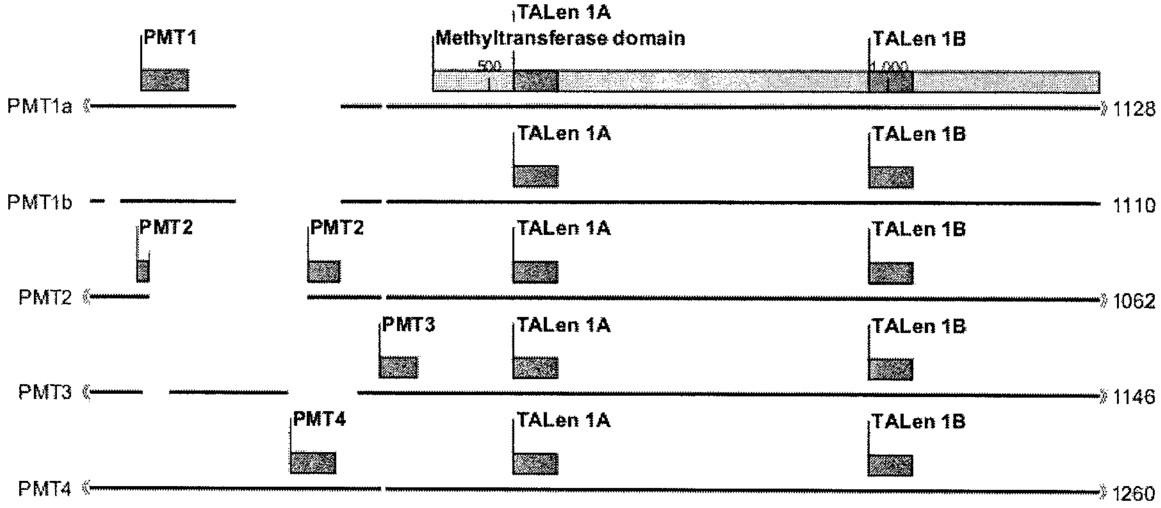
FIG. 5 is a schematic showing exemplary TALEN constructs for site-specific mutagenesis of each of the indicated PMT sequences.

*Locations are shown in FIG. 5

Example 8

Agronomic Practices on Nicotine Reduction

Figure 10:
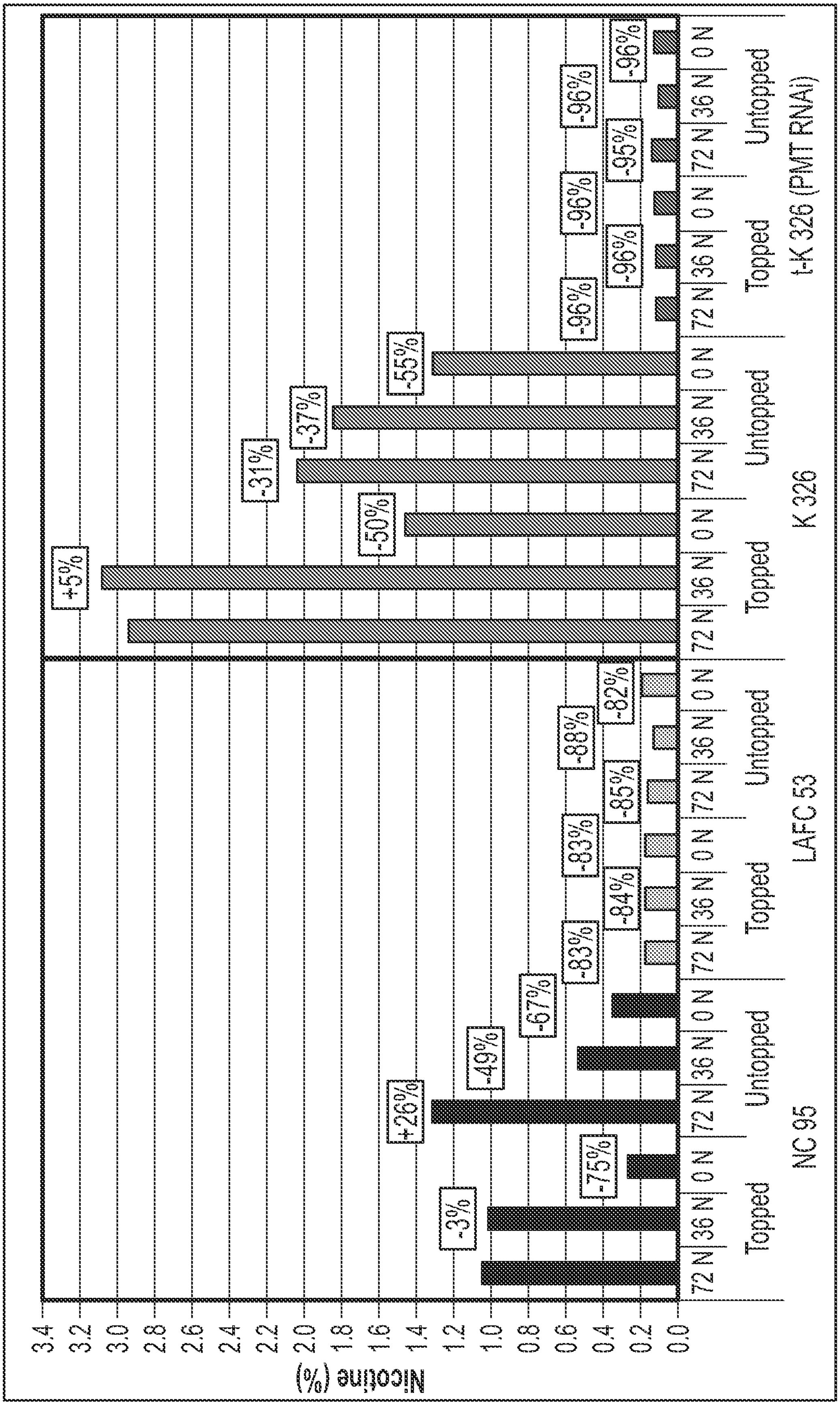
FIG. 10 is a graph showing the impact of agronomic practices on the percent nicotine reduction in selected flue cured lines.

The impact of agronomic practices was examined on the percent nicotine reduction in the flue cured lines, NC95, LAFC 53 (a nic1/nic2 mutant), K326 wild type, and K326 PMT RNAi (a line transgenic for a PMT RNAi). FIG. 10 shows that the K326 PMT RNAi lines exhibited a significant reduction in the amount of nicotine (%) relative to the non-transgenic plants. FIG. 10 also shows that the amount of nicotine in the K326 PMT RNAi lines was reduced to a level comparable to LAFC 53, a mutant line that exhibits extremely low alkaloid content.

Figure 11:
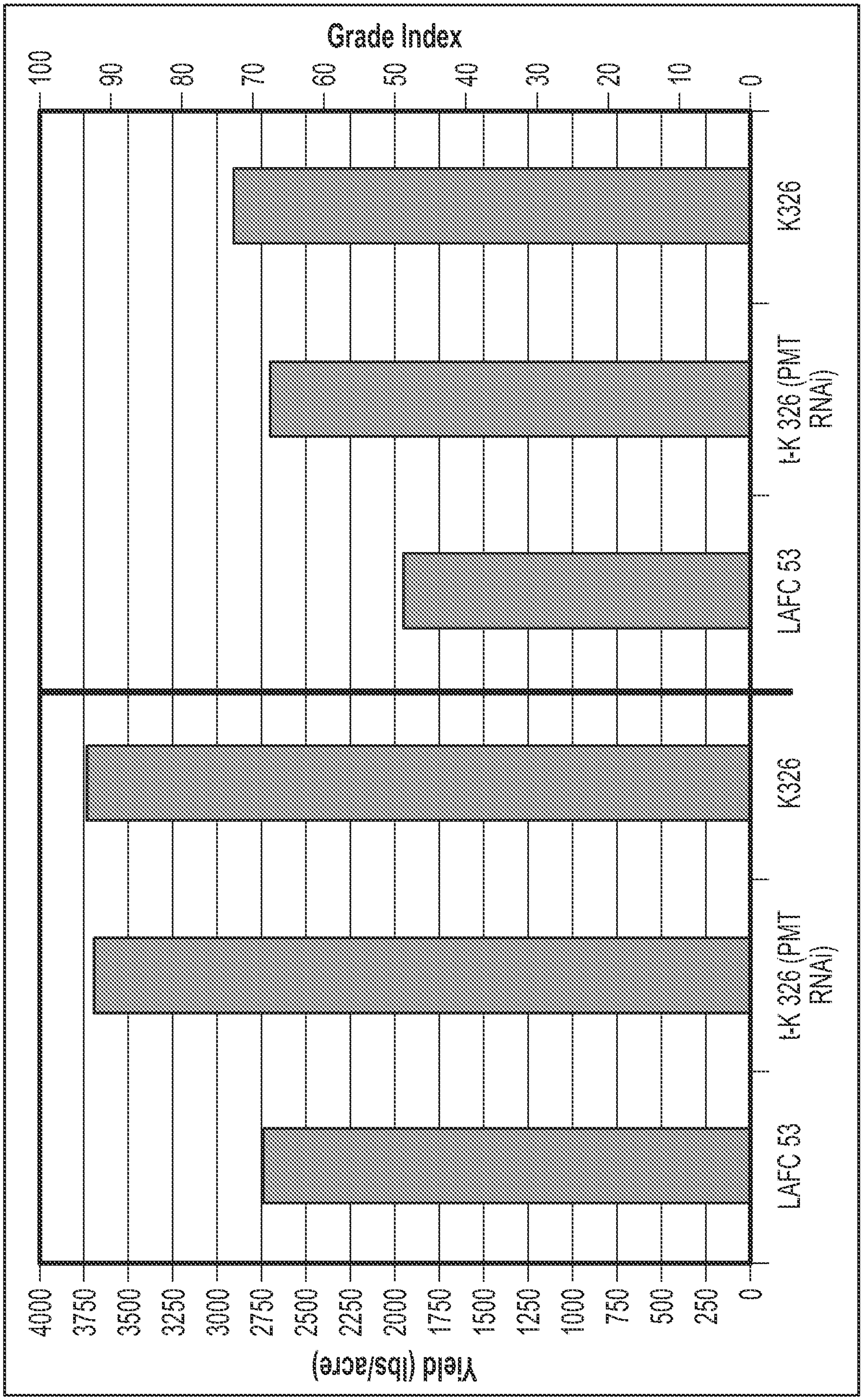
FIG. 11 is a graph showing the yield and leaf quality in selected flue cured varieties.

The yield and leaf quality was examined in the flue cured lines, LAFC 53, K326 PMT-RNAi, and K326. FIG. 11 shows that the K326 PMT RNAi lines exhibited a yield and leaf quality that was similar to the control variety, K326, but exhibited better yield and leaf quality compared to the nic1/nic2 mutant line, LAFC53.

Table 4 shows the alkaloid levels in T1 and T2 generations of K326 PMT RNAi transgenic plants compared to control TN90 plants.

TABLE 4

| Alkaloid levels in T1 and T2 generation PMT RNAi transgenic plants | | | | | | | |
|---|---|---|---|---|---|---|---|
| Variety | Generation | Line ID | Nicotine | Nornicotine | Anabasine | Anatabine | Total Alkaloids |
| K326 PMT RNAi | T1 | T841 | 0.201 ± 0.008 | 0.031 ± 0.009 | 0.0204 ± 0.0038 | 0.319 ± 0.088 | 0.572 ± 0.10 |
| | | Control | 2.73 ± 0.46 | 0.051 ± 0.010 | 0.009 ± 0.0016 | 0.039 ± 0.007 | 2.83 ± 0.47 |
| | T2 | T841 | >0.15 ± 0.0 | 0.0250 ± 0.008 | 0.0178 ± 0.0031 | 0.371 ± 0.068 | 0.414 ± 0.08 |
| | | Control | 2.5 ± 0.28 | 0.048 ± 0.005 | 0.008 ± 0.0012 | 0.049 ± 0.006 | 2.61 ± 0.29 |
| TN90 | T1 | T681 | 0.209 ± 0.02 | 0.058 ± 0.008 | 0.033 ± 0.005 | 0.51 ± 0.163 | 0.809 ± 0.18 |
| | | Control | 4.95 ± 0.56 | 0.104 ± 0.019 | 0.014 ± 0.002 | 0.073 ± 0.011 | 5.14 ± 0.59 |
| | T2 | T681 | >0.15 ± 0.0 | 0.037 ± 0.015 | 0.032 ± 0.009 | 0.555 ± 0.142 | 0.635 ± 0.17 |
| | | Control | 4.12 ± 0.45 | 0.086 ± 0.012 | 0.0146 ± 0.0025 | 0.105 ± 0.014 | 4.33 ± 0.47 |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of generating a transgenic *Nicotiana tabacum* plant comprising:

(a) introducing an RNAi nucleic acid molecule to a *N. tabacum* cell, wherein said RNAi nucleic acid molecule comprises a first nucleic acid sequence at least 95% identical to SEQ ID NO: 11, and a second nucleic acid sequence at least 95% identical to SEQ ID NO: 12, and a spacer nucleic acid comprising a sequence at least 95% identical to SEQ ID NO: 13 between said first nucleic acid sequence and said second nucleic acid sequence;

(b) generating at least one transgenic *N. tabacum* plant from said *N. tabacum* cell; and (c) selecting at least one transgenic *N. tabacum* plant generated in step (b) comprising said RNAi construct, wherein said at least one transgenic *N. tabacum* plant comprises a reduced amount of nicotine as compared to a control plant lacking said RNAi nucleic acid molecule.

2. The method of claim 1, wherein the first nucleic acid sequence is 100% identical to SEQ ID NO: 11.

3. The method of claim 1, wherein the second nucleic acid is 100% identical to SEQ ID NO: 12.

4. The method of claim 1, wherein said RNAi nucleic acid molecule comprises a sequence encoding a promoter that is operable in a plant cell operably linked to said first and second nucleic acid sequences.

5. The method of claim 4, wherein said promoter is selected from the group consisting of a constitutive promoter and a tissue-specific promoter.

6. The method of claim 5, wherein said constitutive promoter is selected from the group consisting of a cassava mosaic virus promoter, a cauliflower mosaic virus 35S promoter, an actin promoter, and a glyceraldehyde-3-phosphate dehydrogenase promoter.

7. The method of claim 5, wherein the tissue-specific promoter is selected from the group consisting of a putrescine N-methyl transferase (PMT) promoter and a quinolinate phosphoribosyltransferase promoter.

8. The method of claim 1, wherein said transgenic *N. tabacum* plant is of a tobacco type selected from the group consisting of a Burley type, a dark type, a flue-cured type, and an Oriental type.

9. The method of claim 1, wherein expression of said RNAi nucleic acid molecule generates a small hairpin RNA molecule.

10. The method of claim 1, wherein said introducing comprises a method selected from the group consisting of electroporation, calcium phosphate precipitation, polyethylene glycol transformation, heat shock, lipofection, microinjection, and viral-mediated nucleic acid transfer.

11. The method of claim 1, wherein the transgenic *N. tabacum* plant comprises a reduction in the amount of a PMT polypeptide comprising the amino acid sequence of SEQ ID NO: 8 as compared to a control *N. tabacum* plant lacking the RNAi nucleic acid molecule.

12. Cured tobacco material comprising leaf from a *Nicotiana tabacum* plant comprising an RNAi nucleic acid molecule, wherein said RNAi nucleic acid molecule comprises a first nucleic acid sequence at least 95% identical to SEQ ID NO: 11, and a second nucleic acid sequence at least 95% identical to SEQ ID NO: 12, and a spacer nucleic acid comprising a sequence at least 95% identical to SEQ ID NO: 13 between said first nucleic acid sequence and said second nucleic acid sequence, and wherein said cured tobacco material comprises a reduced amount of nicotine as compared to cured tobacco material from a control plant lacking said RNAi nucleic acid molecule.

13. The cured tobacco material of claim 12, wherein the cured tobacco material is selected from the group consisting of air cured tobacco material, fire cured tobacco material, flue cured tobacco material, and sun cured tobacco material.

14. The cured tobacco material of claim 12, wherein said leaf comprises a reduced amount of nicotine as compared to leaf from a control plant lacking said RNAi nucleic acid molecule.

15. A tobacco product comprising the cured tobacco material of claim 12.

16. The tobacco product of claim 15 wherein the tobacco product is selected from the group consisting of cigarettes, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, cut tobacco, and snus.

17. The cured tobacco material of claim 12, wherein the first nucleic acid sequence is 100% identical to SEQ ID NO: 11.

18. The cured tobacco material of claim 12, wherein the second nucleic acid is 100% identical to SEQ ID NO: 12.

19. The method of claim 1, wherein the spacer nucleic acid comprises a sequence 100% identical to SEQ ID NO: 13.

20. The cured tobacco material of claim 12, wherein the spacer nucleic acid comprises a sequence 100% identical to SEQ ID NO: 13.

* * * * *

SEQUENCE LISTING

<160> NUMBER OF SEQ ID NOS: 24

<210> SEQ ID NO 1
<211> LENGTH: 1128
<212> TYPE: DNA
<213> ORGANISM: Nicotiana tabacum

<400> SEQUENCE: 1
atggaagtca tatctaccaa cacaaatggc tctaccatct tcaagaatgg tgccattccc 60
atgaacggcc accaaaatgg cacttctgaa cacctcaacg gctaccagaa tggcacttcc 120
aaacaccaaa acgggcacca gaatggcact ttcgaacatc ggaacggcca ccagaatggg 180
acatccgaac aacagaacgg gacaatcagc catgacaatg gcaacgagct actgggaagc 240
tccgactcta ttaagcctgg ctggttttca gagtttagcg cattatggcc aggtgaagca 300
ttctcactta aggttgagaa gttactattc caggggaagt ctgattacca agatgtcatg 360
ctctttgagt cagcaactta tgggaaggtt ctgactttgg atggagcaat tcaacataca 420
gagaatggtg gatttccata cactgaaatg attgttcatc taccacttgg ttccatccca 480
aacccaaaaa aggttttgat catcggcgga ggaattggtt ttacattatt cgaaatgctt 540
cgttatcctt caatcgaaaa aattgacatt gttgagatcg atgacgtggt agttgatgta 600
tccagaaaat tttccctta tctggcagct aattttaacg atcctcgtgt aaccctagtt 660
ctcggagatg gagctgcatt tgtaaaggct gcacaagcgg gatattatga tgctattata 720
gtggactctt ctgatcccat tggtccagca aaagatttgt ttgagaggcc attctttgag 780
gcagtagcca aagcccttag gccaggagga gttgtatgca cacaggctga aagcatttgg 840
cttcatatgc atattattaa gcaaatcatt gctaactgtc gtcaagtctt taagggttct 900
gtcaactatg cttggacaac cgttccaaca tatcccaccg gtgtgatcgg ttatatgctc 960
tgctctactg aagggccaga agttgacttc aagaatccag taaatccaat tgacaaagag 1020
acaactcaag tcaagtccaa attaggacct ctcaagttct acaactctga tattcacaaa 1080
gcagcattca ttttaccatc tttcgccaga agtatgatcg agtcttaa 1128

<210> SEQ ID NO 2
<211> LENGTH: 375
<212> TYPE: PRT
<213> ORGANISM: Nicotiana tabacum

<400> SEQUENCE: 2

Met Glu Val Ile Ser Thr Asn Thr Asn Gly Ser Thr Ile Phe Lys Asn
1 5 10 15

Gly Ala Ile Pro Met Asn Gly His Gln Asn Gly Thr Ser Glu His Leu
20 25 30

Asn Gly Tyr Gln Asn Gly Thr Ser Lys His Gln Asn Gly His Gln Asn
35 40 45

Gly Thr Phe Glu His Arg Asn Gly His Gln Asn Gly Thr Ser Glu Gln
50 55 60

Gln Asn Gly Thr Ile Ser His Asp Asn Gly Asn Glu Leu Leu Gly Ser
65 70 75 80

Ser Asp Ser Ile Lys Pro Gly Trp Phe Ser Glu Phe Ser Ala Leu Trp
85 90 95

Pro Gly Glu Ala Phe Ser Leu Lys Val Glu Lys Leu Leu Phe Gln Gly
100 105 110

Lys Ser Asp Tyr Gln Asp Val Met Leu Phe Glu Ser Ala Thr Tyr Gly
115 120 125

-continued

```
Lys Val Leu Thr Leu Asp Gly Ala Ile Gln His Thr Glu Asn Gly Gly
    130                 135                 140

Phe Pro Tyr Thr Glu Met Ile Val His Leu Pro Leu Gly Ser Ile Pro
145                 150                 155                 160

Asn Pro Lys Lys Val Leu Ile Ile Gly Gly Gly Ile Gly Phe Thr Leu
                165                 170                 175

Phe Glu Met Leu Arg Tyr Pro Ser Ile Glu Lys Ile Asp Ile Val Glu
            180                 185                 190

Ile Asp Asp Val Val Val Asp Val Ser Arg Lys Phe Phe Pro Tyr Leu
        195                 200                 205

Ala Ala Asn Phe Asn Asp Pro Arg Val Thr Leu Val Leu Gly Asp Gly
    210                 215                 220

Ala Ala Phe Val Lys Ala Ala Gln Ala Gly Tyr Tyr Asp Ala Ile Ile
225                 230                 235                 240

Val Asp Ser Ser Asp Pro Ile Gly Pro Ala Lys Asp Leu Phe Glu Arg
                245                 250                 255

Pro Phe Phe Glu Ala Val Ala Lys Ala Leu Arg Pro Gly Gly Val Val
            260                 265                 270

Cys Thr Gln Ala Glu Ser Ile Trp Leu His Met His Ile Ile Lys Gln
        275                 280                 285

Ile Ile Ala Asn Cys Arg Gln Val Phe Lys Gly Ser Val Asn Tyr Ala
    290                 295                 300

Trp Thr Thr Val Pro Thr Tyr Pro Thr Gly Val Ile Gly Tyr Met Leu
305                 310                 315                 320

Cys Ser Thr Glu Gly Pro Glu Val Asp Phe Lys Asn Pro Val Asn Pro
                325                 330                 335

Ile Asp Lys Glu Thr Thr Gln Val Lys Ser Lys Leu Gly Pro Leu Lys
            340                 345                 350

Phe Tyr Asn Ser Asp Ile His Lys Ala Ala Phe Ile Leu Pro Ser Phe
        355                 360                 365

Ala Arg Ser Met Ile Glu Ser
    370                 375
```

<210> SEQ ID NO 3
<211> LENGTH: 1110
<212> TYPE: DNA
<213> ORGANISM: Nicotiana tabacum

<400> SEQUENCE: 3

```
atggaagtca tatctaccat cttcaagaat ggtaccattc ccatgaacgg ccaccaaaat      60

ggctcttccg aacacctcaa cggctaccag aatggcattt ccaaacacca aaacgggcac     120

cagaatggca cttccgaaca tcggaacggc caccagaatg ggacatccga acaacagaac     180

gggacaatca gccatgacaa tggcaacgag ctactgggaa gctccaactc tattaagcct     240

ggttggtttt cagagtttag cgcattatgg ccaggtgaag cattctcact taaggtcgag     300

aagttactat tccaggggaa atctgattac caagatgtca tgctctttga gtcagcaact     360

tatgggaagg ttctgacttt ggatggagca attcaacata cagagaatgg tggatttcca     420

tacactgaaa tgattgttca tctaccactt ggttccatcc caaacccaaa aaaggttttg     480

atcatcggcg gaggaattgg ttttacatta ttcgaaatgc ttcgttatcc ttcaatcgaa     540

aaaattgaca ttgttgagat cgatgacgtg gtagttgatg tatccagaaa atttttccct     600

tatctggcag ctaattttaa cgatcctcgt gtaaccctag ttctcggaga tggagctgca     660
```

-continued

```
tttgtaaagg ctgcacaagc gggatattat gatgctatta tagtggactc ttctgatccc    720
attggtccag caaaagattt gtttgagagg ccattctttg aggcagtagc caaagccctt    780
aggccaggag gagttgtatg cacacaggct gaaagcattt ggcttcatat gcatattatt    840
aagcaaatca ttgctaactg tcgtcaagtc tttaagggtt ctgtcaacta tgcttggaca    900
accgttccaa catatcccac cggtgtgatt ggttatatgc tctgctctac tgaagggcca    960
gaagttaact tcaagaatcc agtaaatcca attgacaaag agacaactca agtcaagtcc   1020
aaattaggac ctctcaagtt ctacaactct gatattcaca aagcagcatt cattttgcca   1080
tctttcgccc gaagtatgat cgagtcttaa                                    1110

<210> SEQ ID NO 4
<211> LENGTH: 369
<212> TYPE: PRT
<213> ORGANISM: Nicotiana tabacum

<400> SEQUENCE: 4

Met Glu Val Ile Ser Thr Ile Phe Lys Asn Gly Thr Ile Pro Met Asn
1               5                   10                  15

Gly His Gln Asn Gly Ser Ser Glu His Leu Asn Gly Tyr Gln Asn Gly
            20                  25                  30

Ile Ser Lys His Gln Asn Gly His Gln Asn Gly Thr Ser Glu His Arg
        35                  40                  45

Asn Gly His Gln Asn Gly Thr Ser Glu Gln Gln Asn Gly Thr Ile Ser
    50                  55                  60

His Asp Asn Gly Asn Glu Leu Leu Gly Ser Ser Asn Ser Ile Lys Pro
65                  70                  75                  80

Gly Trp Phe Ser Glu Phe Ser Ala Leu Trp Pro Gly Glu Ala Phe Ser
                85                  90                  95

Leu Lys Val Glu Lys Leu Leu Phe Gln Gly Lys Ser Asp Tyr Gln Asp
            100                 105                 110

Val Met Leu Phe Glu Ser Ala Thr Tyr Gly Lys Val Leu Thr Leu Asp
        115                 120                 125

Gly Ala Ile Gln His Thr Glu Asn Gly Gly Phe Pro Tyr Thr Glu Met
    130                 135                 140

Ile Val His Leu Pro Leu Gly Ser Ile Pro Asn Pro Lys Lys Val Leu
145                 150                 155                 160

Ile Ile Gly Gly Gly Ile Gly Phe Thr Leu Phe Glu Met Leu Arg Tyr
                165                 170                 175

Pro Ser Ile Glu Lys Ile Asp Ile Val Glu Ile Asp Asp Val Val Val
            180                 185                 190

Asp Val Ser Arg Lys Phe Phe Pro Tyr Leu Ala Ala Asn Phe Asn Asp
        195                 200                 205

Pro Arg Val Thr Leu Val Leu Gly Asp Gly Ala Ala Phe Val Lys Ala
    210                 215                 220

Ala Gln Ala Gly Tyr Tyr Asp Ala Ile Ile Val Asp Ser Ser Asp Pro
225                 230                 235                 240

Ile Gly Pro Ala Lys Asp Leu Phe Glu Arg Pro Phe Phe Glu Ala Val
                245                 250                 255

Ala Lys Ala Leu Arg Pro Gly Gly Val Val Cys Thr Gln Ala Glu Ser
            260                 265                 270

Ile Trp Leu His Met His Ile Ile Lys Gln Ile Ile Ala Asn Cys Arg
        275                 280                 285

Gln Val Phe Lys Gly Ser Val Asn Tyr Ala Trp Thr Thr Val Pro Thr
```

```
    290                 295                 300

Tyr Pro Thr Gly Val Ile Gly Tyr Met Leu Cys Ser Thr Glu Gly Pro
305                 310                 315                 320

Glu Val Asn Phe Lys Asn Pro Val Asn Pro Ile Asp Lys Glu Thr Thr
                325                 330                 335

Gln Val Lys Ser Lys Leu Gly Pro Leu Lys Phe Tyr Asn Ser Asp Ile
            340                 345                 350

His Lys Ala Ala Phe Ile Leu Pro Ser Phe Ala Arg Ser Met Ile Glu
        355                 360                 365

Ser
```

```
<210> SEQ ID NO 5
<211> LENGTH: 1062
<212> TYPE: DNA
<213> ORGANISM: Nicotiana tabacum

<400> SEQUENCE: 5

atggaagtca tatctaccaa cacaaatggc tctaccatct tcaagagtgg tgccattccc      60

atgaatggcc accataatgg cacttccaaa caccaaaacg gccacaagaa tgggacttcc     120

gaacaacaga acgggacaat cagccttgat aatggcaacg agctactggg aaactccaat     180

tgtattaagc ctggttggtt ttcagagttt agcgcattat ggccaggtga agcattctca     240

cttaaggttg agaagttact gttccagggg aagtctgact accaagatgt catgctcttt     300

gagtcagcaa cttatgggaa ggttctgact ttggatggag caattcaaca cacagagaat     360

ggtggatttc catacactga aatgattgtt catcttccac ttggttccat cccaaaccca     420

aaaaaggttt tgatcatcgg cggaggaatt ggttttacat tattcgaaat gcttcgttat     480

cctacaatcg aaaaaattga cattgttgag atcgatgacg tggtagttga tgtatctaga     540

aaatttttcc cttatctcgc tgctaatttt aacgatcctc gtgtaaccct agtccttgga     600

gatggggctg catttgtaaa ggctgcacaa gcagaatatt atgatgctat tatagtggac     660

tcttctgatc ccattggtcc agcaaaagat ttgtttgaga ggccattctt tgaggcagta     720

gctaaagccc taaggccagg aggagttgta tgcacacagg ctgaaagcat ttggcttcat     780

atgcatatta ttaagcaaat cattgctaac tgtcgtcaag tctttaaggg ctctgtcaac     840

tatgcttgga ctactgttcc aacatatcca accggtgtga ttggttatat gctctgctct     900

actgaaggac cagaaattga cttcaagaat ccagtaaatc caattgacaa agagacagct     960

caagtcaagt ccaaattagc acctctcaag ttctacaact ctgatattca caaagcagca    1020

ttcattttgc catctttcgc cagaagtatg atcgagtctt aa                       1062
```

```
<210> SEQ ID NO 6
<211> LENGTH: 353
<212> TYPE: PRT
<213> ORGANISM: Nicotiana tabacum

<400> SEQUENCE: 6

Met Glu Val Ile Ser Thr Asn Thr Asn Gly Ser Thr Ile Phe Lys Ser
1               5                   10                  15

Gly Ala Ile Pro Met Asn Gly His His Asn Gly Thr Ser Lys His Gln
            20                  25                  30

Asn Gly His Lys Asn Gly Thr Ser Glu Gln Gln Asn Gly Thr Ile Ser
        35                  40                  45

Leu Asp Asn Gly Asn Glu Leu Leu Gly Asn Ser Asn Cys Ile Lys Pro
    50                  55                  60
```

```
Gly Trp Phe Ser Glu Phe Ser Ala Leu Trp Pro Gly Glu Ala Phe Ser
65                  70                  75                  80

Leu Lys Val Glu Lys Leu Leu Phe Gln Gly Lys Ser Asp Tyr Gln Asp
                85                  90                  95

Val Met Leu Phe Glu Ser Ala Thr Tyr Gly Lys Val Leu Thr Leu Asp
            100                 105                 110

Gly Ala Ile Gln His Thr Glu Asn Gly Gly Phe Pro Tyr Thr Glu Met
        115                 120                 125

Ile Val His Leu Pro Leu Gly Ser Ile Pro Asn Pro Lys Lys Val Leu
    130                 135                 140

Ile Ile Gly Gly Gly Ile Gly Phe Thr Leu Phe Glu Met Leu Arg Tyr
145                 150                 155                 160

Pro Thr Ile Glu Lys Ile Asp Ile Val Glu Ile Asp Asp Val Val Val
                165                 170                 175

Asp Val Ser Arg Lys Phe Phe Pro Tyr Leu Ala Ala Asn Phe Asn Asp
            180                 185                 190

Pro Arg Val Thr Leu Val Leu Gly Asp Gly Ala Ala Phe Val Lys Ala
        195                 200                 205

Ala Gln Ala Glu Tyr Tyr Asp Ala Ile Ile Val Asp Ser Ser Asp Pro
    210                 215                 220

Ile Gly Pro Ala Lys Asp Leu Phe Glu Arg Pro Phe Phe Glu Ala Val
225                 230                 235                 240

Ala Lys Ala Leu Arg Pro Gly Gly Val Val Cys Thr Gln Ala Glu Ser
                245                 250                 255

Ile Trp Leu His Met His Ile Ile Lys Gln Ile Ile Ala Asn Cys Arg
            260                 265                 270

Gln Val Phe Lys Gly Ser Val Asn Tyr Ala Trp Thr Thr Val Pro Thr
        275                 280                 285

Tyr Pro Thr Gly Val Ile Gly Tyr Met Leu Cys Ser Thr Glu Gly Pro
    290                 295                 300

Glu Ile Asp Phe Lys Asn Pro Val Asn Pro Ile Asp Lys Glu Thr Ala
305                 310                 315                 320

Gln Val Lys Ser Lys Leu Ala Pro Leu Lys Phe Tyr Asn Ser Asp Ile
                325                 330                 335

His Lys Ala Ala Phe Ile Leu Pro Ser Phe Ala Arg Ser Met Ile Glu
            340                 345                 350

Ser


<210> SEQ ID NO 7
<211> LENGTH: 1146
<212> TYPE: DNA
<213> ORGANISM: Nicotiana tabacum

<400> SEQUENCE: 7

atggaagtca tatctaccaa cacaaatggc tctactatct tcaagaatgg tgccattccc      60

atgaacggtt accagaatgg cacttccaaa caccaaaacg gccaccagaa tggcacttcc     120

gaacatcgga acggccacca gaatgggatt tccgaacacc aaaacggcca ccagaatggc     180

acttccgagc atcagaacgg ccatcagaat gggacaatca gccatgacaa cggcaacgag     240

ctacagctac tgggaagctc caactctatt aagcctggtt ggttttcaga gtttagcgca     300

ttatggccag gtgaagcatt ctcacttaag gttgagaagt tactattcca ggggaagtct     360

gattaccaag atgtcatgct ctttgagtca gcaacatatg ggaaggttct gactttggat     420
```

-continued

```
ggagcaattc aacacacaga gaatggtgga tttccataca ctgaaatgat tgttcatctt    480

ccacttggtt ccatcccaaa ccctaaaaag gttttgatca tcggcggagg aattggtttt    540

acattattcg aaatgcttcg ttatcctaca atcgaaaaaa ttgacattgt tgagatcgat    600

gacgtggtag ttgatgtatc tagaaaattt ttcccttatc ttgctgctaa ttttagcgat    660

cctcgtgtaa ccctagtcct tggagatggg gctgcatttg taaaggccgc acaagcagga    720

tattatgatg ctattatagt ggactcttct gatcccattg gtccagcaaa agacttgttt    780

gagaggccat tctttgaggc agtagccaaa gccctaaggc caggaggagt tgtatgcaca    840

caggctgaaa gcatttggct tcatatgcat attattaagc aaatcattgc taactgtcgt    900

caagtcttta agggctctgt caactatgct tggactactg ttccaacata tccaaccggt    960

gtgattggtt atatgctctg ttctactgaa ggaccagaag ttgacttcaa gaatccagta   1020

aatccaattg acaaagagac aactcaagtc aagtccaaat tagcacctct caagttctac   1080

aactctgata ttcacaaagc agcattcatt ttgccatctt tcgccagaag tatgatcgag   1140

tcttaa                                                              1146
```

<210> SEQ ID NO 8
<211> LENGTH: 381
<212> TYPE: PRT
<213> ORGANISM: Nicotiana tabacum

<400> SEQUENCE: 8

```
Met Glu Val Ile Ser Thr Asn Thr Asn Gly Ser Thr Ile Phe Lys Asn
1               5                   10                  15

Gly Ala Ile Pro Met Asn Gly Tyr Gln Asn Gly Thr Ser Lys His Gln
            20                  25                  30

Asn Gly His Gln Asn Gly Thr Ser Glu His Arg Asn Gly His Gln Asn
        35                  40                  45

Gly Ile Ser Glu His Gln Asn Gly His Gln Asn Gly Thr Ser Glu His
    50                  55                  60

Gln Asn Gly His Gln Asn Gly Thr Ile Ser His Asp Asn Gly Asn Glu
65                  70                  75                  80

Leu Gln Leu Leu Gly Ser Ser Asn Ser Ile Lys Pro Gly Trp Phe Ser
                85                  90                  95

Glu Phe Ser Ala Leu Trp Pro Gly Glu Ala Phe Ser Leu Lys Val Glu
            100                 105                 110

Lys Leu Leu Phe Gln Gly Lys Ser Asp Tyr Gln Asp Val Met Leu Phe
        115                 120                 125

Glu Ser Ala Thr Tyr Gly Lys Val Leu Thr Leu Asp Gly Ala Ile Gln
    130                 135                 140

His Thr Glu Asn Gly Gly Phe Pro Tyr Thr Glu Met Ile Val His Leu
145                 150                 155                 160

Pro Leu Gly Ser Ile Pro Asn Pro Lys Lys Val Leu Ile Ile Gly Gly
                165                 170                 175

Gly Ile Gly Phe Thr Leu Phe Glu Met Leu Arg Tyr Pro Thr Ile Glu
            180                 185                 190

Lys Ile Asp Ile Val Glu Ile Asp Asp Val Val Val Asp Val Ser Arg
        195                 200                 205

Lys Phe Phe Pro Tyr Leu Ala Ala Asn Phe Ser Asp Pro Arg Val Thr
    210                 215                 220

Leu Val Leu Gly Asp Gly Ala Ala Phe Val Lys Ala Ala Gln Ala Gly
225                 230                 235                 240
```

```
Tyr Tyr Asp Ala Ile Ile Val Asp Ser Ser Asp Pro Ile Gly Pro Ala
                245                 250                 255

Lys Asp Leu Phe Glu Arg Pro Phe Phe Glu Ala Val Ala Lys Ala Leu
            260                 265                 270

Arg Pro Gly Gly Val Val Cys Thr Gln Ala Glu Ser Ile Trp Leu His
        275                 280                 285

Met His Ile Ile Lys Gln Ile Ile Ala Asn Cys Arg Gln Val Phe Lys
    290                 295                 300

Gly Ser Val Asn Tyr Ala Trp Thr Thr Val Pro Thr Tyr Pro Thr Gly
305                 310                 315                 320

Val Ile Gly Tyr Met Leu Cys Ser Thr Glu Gly Pro Glu Val Asp Phe
                325                 330                 335

Lys Asn Pro Val Asn Pro Ile Asp Lys Glu Thr Thr Gln Val Lys Ser
            340                 345                 350

Lys Leu Ala Pro Leu Lys Phe Tyr Asn Ser Asp Ile His Lys Ala Ala
        355                 360                 365

Phe Ile Leu Pro Ser Phe Ala Arg Ser Met Ile Glu Ser
    370                 375                 380
```

<210> SEQ ID NO 9
<211> LENGTH: 1260
<212> TYPE: DNA
<213> ORGANISM: Nicotiana tabacum

<400> SEQUENCE: 9

```
atggaagtca tatctaccaa cacaaatggc tcgaccatct tcaagaatgg tgccattccc     60

atgaatggcc accagagtgg cacttccaaa cacctcaacg gctaccagaa cggcacttcc    120

aaacaccaaa acggccacca taatggcact tccgaacatc ggaacggcca ccagaatggg    180

atttccgaac accaaaacgg ccaccagaat gggacttccg aacatcggaa cggccaccag    240

aatgggattt ccgaacacca aaacggccac cagaatggga cttccgaaca ccaaaacggc    300

caccagaatg ggacttccga acaacagaac gggacaatca gccatgacaa tggcaacgag    360

ctactgggaa actccaactc tattaagctt ggttggtttt cagagtttag cgcattatgg    420

ccaggtgaag cattctccct taaggttgag aagttactat ttcaggggaa gtctgactac    480

caagatgtca tgctctttga gtcagcaaca tatgggaagg ttttgacttt ggatggagca    540

attcaacaca cagagaatgg tggatttcca tacactgaaa tgattgttca tcttccactt    600

ggttccatcc caaacccaaa aaaggttttg atcatcggcg gaggaattgg ttttacatta    660

ttcgaaatgc ttcgttatcc tacaatcgaa aaaattgaca ttgttgaaat cgatgacgtg    720

gtagttgatg tatctagaaa atctttccct tatctcgcag ctaattttaa tgatcctcgt    780

gtaaccctcg ttctcggaga tggggctgca tttgtaaagg ctgcacaagc aggatattat    840

gatgctatta tagtggactc ttctgatccc attggtccag caaaagattt gtttgagagg    900

ccattctttg aggcagtagc caaagcccta aggccaggag gagttgtatg cacacaggcc    960

gaaagcattt ggcttcatat gcatattatt aagcaaatca ttgctaactg tcgtcaagtc   1020

tttaagggct ctgtcaacta cgcttggact actgttccaa catatcccac tggtgtaatt   1080

gggtatatgc tctgctctac tgaagggcca gaagttgact tcaagaatcc aataaatcca   1140

attgacaaag agacaactca agtcaagtcc aaattagcac ctctcaagtt ttacaattct   1200

gatattcaca aagcagcatt cattttgcca tctttcgcca gaagtatgat cgagtcttaa   1260
```

<210> SEQ ID NO 10

<211> LENGTH: 419
<212> TYPE: PRT
<213> ORGANISM: Nicotiana tabacum

<400> SEQUENCE: 10

```
Met Glu Val Ile Ser Thr Asn Thr Asn Gly Ser Thr Ile Phe Lys Asn
1               5                   10                  15

Gly Ala Ile Pro Met Asn Gly His Gln Ser Gly Thr Ser Lys His Leu
            20                  25                  30

Asn Gly Tyr Gln Asn Gly Thr Ser Lys His Gln Asn Gly His His Asn
        35                  40                  45

Gly Thr Ser Glu His Arg Asn Gly His Gln Asn Gly Ile Ser Glu His
    50                  55                  60

Gln Asn Gly His Gln Asn Gly Thr Ser Glu His Arg Asn Gly His Gln
65                  70                  75                  80

Asn Gly Ile Ser Glu His Gln Asn Gly His Gln Asn Gly Thr Ser Glu
                85                  90                  95

His Gln Asn Gly His Gln Asn Gly Thr Ser Glu Gln Gln Asn Gly Thr
            100                 105                 110

Ile Ser His Asp Asn Gly Asn Glu Leu Leu Gly Asn Ser Asn Ser Ile
        115                 120                 125

Lys Leu Gly Trp Phe Ser Glu Phe Ser Ala Leu Trp Pro Gly Glu Ala
    130                 135                 140

Phe Ser Leu Lys Val Glu Lys Leu Leu Phe Gln Gly Lys Ser Asp Tyr
145                 150                 155                 160

Gln Asp Val Met Leu Phe Glu Ser Ala Thr Tyr Gly Lys Val Leu Thr
                165                 170                 175

Leu Asp Gly Ala Ile Gln His Thr Glu Asn Gly Gly Phe Pro Tyr Thr
            180                 185                 190

Glu Met Ile Val His Leu Pro Leu Gly Ser Ile Pro Asn Pro Lys Lys
        195                 200                 205

Val Leu Ile Ile Gly Gly Gly Ile Gly Phe Thr Leu Phe Glu Met Leu
    210                 215                 220

Arg Tyr Pro Thr Ile Glu Lys Ile Asp Ile Val Glu Ile Asp Asp Val
225                 230                 235                 240

Val Val Asp Val Ser Arg Lys Ser Phe Pro Tyr Leu Ala Ala Asn Phe
                245                 250                 255

Asn Asp Pro Arg Val Thr Leu Val Leu Gly Asp Gly Ala Ala Phe Val
            260                 265                 270

Lys Ala Ala Gln Ala Gly Tyr Tyr Asp Ala Ile Ile Val Asp Ser Ser
        275                 280                 285

Asp Pro Ile Gly Pro Ala Lys Asp Leu Phe Glu Arg Pro Phe Phe Glu
    290                 295                 300

Ala Val Ala Lys Ala Leu Arg Pro Gly Gly Val Val Cys Thr Gln Ala
305                 310                 315                 320

Glu Ser Ile Trp Leu His Met His Ile Ile Lys Gln Ile Ile Ala Asn
                325                 330                 335

Cys Arg Gln Val Phe Lys Gly Ser Val Asn Tyr Ala Trp Thr Thr Val
            340                 345                 350

Pro Thr Tyr Pro Thr Gly Val Ile Gly Tyr Met Leu Cys Ser Thr Glu
        355                 360                 365

Gly Pro Glu Val Asp Phe Lys Asn Pro Ile Asn Pro Ile Asp Lys Glu
    370                 375                 380

Thr Thr Gln Val Lys Ser Lys Leu Ala Pro Leu Lys Phe Tyr Asn Ser
```

385 390 395 400

Asp Ile His Lys Ala Ala Phe Ile Leu Pro Ser Phe Ala Arg Ser Met
405 410 415

Ile Glu Ser

<210> SEQ ID NO 11
<211> LENGTH: 500
<212> TYPE: DNA
<213> ORGANISM: Artificial Sequence
<220> FEATURE:
<223> OTHER INFORMATION: Synthetic oligonucleotides

<400> SEQUENCE: 11
accaacacaa atggctctac tatcttcaag aatggtgcca ttcccatgaa cggttaccag 60
aatggcactt ccaaacacca aaacggccac cagaatggca cttccgaaca tcggaacggc 120
caccagaatg ggatttccga acaccaaaac ggccaccaga atggcacttc cgagcatcag 180
aacggccatc agaatgggac aatcagccat gacaacggca acgagctaca gctactggga 240
agctccaact ctattaagcc tggttggttt tcagagttta gcgcattatg gccaggtgaa 300
gcattctcac ttaaggttga gaagttacta ttccagggga agtctgatta ccaagatgtc 360
atgctctttg agtcagcaac atatgggaag gttctgactt tggatggagc aattcaacac 420
acagagaatg gtggatttcc atacactgaa atgattgttc atcttccact tggttccatc 480
ccaaacccta aaaaggtttt 500

<210> SEQ ID NO 12
<211> LENGTH: 500
<212> TYPE: DNA
<213> ORGANISM: Artificial Sequence
<220> FEATURE:
<223> OTHER INFORMATION: Synthetic oligonucleotides

<400> SEQUENCE: 12
aaaacctttt tagggtttgg gatggaacca agtggaagat gaacaatcat ttcagtgtat 60
ggaaatccac cattctctgt gtgttgaatt gctccatcca aagtcagaac cttcccatat 120
gttgctgact caaagagcat gacatcttgg taatcagact tcccctggaa tagtaacttc 180
tcaaccttaa gtgagaatgc ttcacctggc cataatgcgc taaactctga aaaccaacca 240
ggcttaatag agttggagct tcccagtagc tgtagctcgt tgccgttgtc atggctgatt 300
gtcccattct gatggccgtt ctgatgctcg gaagtgccat tctggtggcc gttttggtgt 360
tcggaaatcc cattctggtg gccgttccga tgttcggaag tgccattctg gtggccgttt 420
tggtgtttgg aagtgccatt ctggtaaccg ttcatgggaa tggcaccatt cttgaagata 480
gtagagccat ttgtgttggt 500

<210> SEQ ID NO 13
<211> LENGTH: 672
<212> TYPE: DNA
<213> ORGANISM: Artificial Sequence
<220> FEATURE:
<223> OTHER INFORMATION: Synthetic oligonucleotides

<400> SEQUENCE: 13
gaattcggtg agttcccccc tcctcccctt tcacttttgt ttgttggttt ctaagtgctc 60
tttcaattta gaggttgatg ttgggaaata attaaacaat actcttgttt tctaaaattt 120
cttgaaaact acaatgtcta tagaggcaat atatttgctt ctaaacgttg acggttttgc 180
aagtcttgcg gaggagcttt gatccagtgt taaagaaata tatcatgtct cttattcatc 240
ctccctttct ttcctttgtg ttttgcttca ctcctggggt ttcaactttt ttctttccgt 300
ttaacctttc cttttttctg caggatggaa cttcaaatta ctttaaagga ctgatgctcc 360
ttctctgcta ttgatagttg ctgcaagttt ctttgtgcat atagatccag agtctatacg 420
taagttgtgt ttctttttcg tgaaattacc atatgacatt gacagctcct ggtcttcgtt 480
ttatttattc ttttggtgtt ccttttaacc gataacatct gttattattt cactgttaca 540
ctaatctgct ttgcttatgg tcagtcagtt tagcattaga ttagataacc agttaaccat 600
tttgggtctc gttaacgtaa tattgtattg ataactacct tatcatatat atatctctgt 660
tttagtgaat tc 672

<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotides

<400> SEQUENCE: 14
attctagacc aacacaaatg gctctac 27

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotides

<400> SEQUENCE: 15
ataagcttaa aaccttttta gggtttgg 28

<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotides

<400> SEQUENCE: 16
atgagctcac caacacaaat ggctctac 28

<210> SEQ ID NO 17
<211> LENGTH: 28
<212> TYPE: DNA
<213> ORGANISM: Artificial Sequence
<220> FEATURE:
<223> OTHER INFORMATION: Synthetic oligonucleotides

<400> SEQUENCE: 17
atggatccaa aacctttttta gggtttgg 28

<210> SEQ ID NO 18
<211> LENGTH: 56
<212> TYPE: DNA
<213> ORGANISM: Artificial Sequence
<220> FEATURE:
<223> OTHER INFORMATION: Synthetic oligonucleotides

<400> SEQUENCE: 18
tgaaatgatt gttcatctac cacttggttc catcccaaac ccaaaaaagg ttttga 56

<210> SEQ ID NO 19
<211> LENGTH: 55
<212> TYPE: DNA
<213> ORGANISM: Artificial Sequence
<220> FEATURE:
<223> OTHER INFORMATION: Synthetic oligonucleotides

<400> SEQUENCE: 19
taaatccaat tgacaaagag acaactcaag tcaagtccaa attaggacct ctcaa 55

<210> SEQ ID NO 20
<211> LENGTH: 54
<212> TYPE: DNA
<213> ORGANISM: Artificial Sequence
<220> FEATURE:
<223> OTHER INFORMATION: Synthetic oligonucleotides

<400> SEQUENCE: 20
tgaacggcca ccaaaatggc acttctgaac acctcaacgg ctaccagaat ggca 54

<210> SEQ ID NO 21
<211> LENGTH: 59
<212> TYPE: DNA
<213> ORGANISM: Artificial Sequence
<220> FEATURE:
<223> OTHER INFORMATION: Synthetic oligonucleotides

<400> SEQUENCE: 21
tcccatgaat ggccaccata atggcacttc caaacaccaa aacggccaca agaatggga 59

<210> SEQ ID NO 22
<211> LENGTH: 49
<212> TYPE: DNA
<213> ORGANISM: Artificial Sequence
<220> FEATURE:
<223> OTHER INFORMATION: Synthetic oligonucleotides

<400> SEQUENCE: 22
tacagctact gggaagctcc aactctatta agcctggttg gttttcaga 49

<210> SEQ ID NO 23
<211> LENGTH: 58
<212> TYPE: DNA
<213> ORGANISM: Artificial Sequence
<220> FEATURE:
<223> OTHER INFORMATION: Synthetic oligonucleotides

<400> SEQUENCE: 23
tccgaacacc aaaacggcca ccagaatggg acttccgaac accaaaacgg ccaccaga 58

<210> SEQ ID NO 24
<211> LENGTH: 496
<212> TYPE: DNA
<213> ORGANISM: Artificial Sequence
<220> FEATURE:
<223> OTHER INFORMATION: Synthetic oligonucleotides

<400> SEQUENCE: 24
ccaacacaaa tggctctact atcttcaaga atggtgccat tcccatgaac ggttaccaga 60
atggcacttc caaacaccaa aacggccacc agaatggcac ttccgaacat cggaacggcc 120
accagaatgg gatttccgaa caccaaaacg gccaccagaa tggcacttcc gagcatcaga 180
acggccatca gaatgggaca atcagccatg acaacggcaa cgagctacag ctactgggaa 240
gctccaactc tattaagcct ggttggtttt cagagtttag cgcattatgg ccaggtgaag 300

-continued

```
cattctcact taaggttgag aagttactat tccaggggaa gtctgattac caagatgtca    360

tgctctttga gtcagcaaca tatgggaagg ttctgacttt ggatggagca atcaacacac    420

agagaatggt ggatttccat acactgaaat gatgttcatc ttccacttgg ttccatccca    480

aaccctaaaa agtttt                                                    496
```